United States Patent
Lachaine et al.

(10) Patent No.: US 11,040,221 B2
(45) Date of Patent: Jun. 22, 2021

(54) ADAPTIVE RADIATION THERAPY USING COMPOSITE IMAGING SLICES

(71) Applicant: Elekta LTD., Montreal (CA)

(72) Inventors: Martin Emile Lachaine, Montreal (CA); Francois Paul George Rene Hebert, Montreal (CA)

(73) Assignee: Elekta LTD., Montreal (CA)

( * ) Notice: Subject to any disclaimer, the term of this patent is extended or adjusted under 35 U.S.C. 154(b) by 0 days.

(21) Appl. No.: 16/824,276

(22) Filed: Mar. 19, 2020

(65) Prior Publication Data
US 2021/0046329 A1  Feb. 18, 2021

Related U.S. Application Data

(60) Provisional application No. 62/886,030, filed on Aug. 13, 2019.

(51) Int. Cl.
*A61B 6/00* (2006.01)
*A61N 5/10* (2006.01)
(Continued)

(52) U.S. Cl.
CPC ......... *A61N 5/1049* (2013.01); *A61N 5/1039* (2013.01); *A61N 5/1067* (2013.01);
(Continued)

(58) Field of Classification Search
CPC combination set(s) only.
See application file for complete search history.

(56) References Cited

U.S. PATENT DOCUMENTS

| 6,480,732 B1 | 11/2002 | Tanaka et al. |
| 7,496,174 B2 | 2/2009 | Gertner et al. |
| (Continued) | | |

FOREIGN PATENT DOCUMENTS

| EP | 2664360 A2 | 11/2013 |
| WO | WO-2018048507 A1 | 3/2018 |
| WO | 2018161123 | 9/2018 |

OTHER PUBLICATIONS

Ginn, John S., "Model-Interpolated Gating for Magnetic Resonance ImageeGuided Radiation Therapy", Imaging in Radiation Oncology, (May 2, 2018), 10 pgs.
(Continued)

*Primary Examiner* — Joel F Brutus
(74) *Attorney, Agent, or Firm* — Schwegman Lundberg & Woessner, P.A.; Sanjay Agrawal

(57) ABSTRACT

Systems and methods are provided for registering images. The systems and methods perform operations comprising: receiving, at a first time point during a given radiation session, a first imaging slice comprising an object, the first imaging slice corresponding to a first plane; accessing, at the first time point during the given radiation session, a composite imaging slice corresponding to the first plane, the composite imaging slice being generated using a plurality of imaging slices obtained prior to the first time point; spatially registering the first imaging slice and the composite imaging slice; determining movement of the object using the spatially registered first imaging slice and the composite imaging slice; and generating an updated therapy protocol to control delivery of a therapy beam based on the determined movement.

34 Claims, 22 Drawing Sheets

(51) Int. Cl.

| | | |
|---|---|---|
| *G06T 7/33* | (2017.01) | |
| *G16H 40/63* | (2018.01) | |
| *G16H 20/40* | (2018.01) | |
| *G16H 30/20* | (2018.01) | |
| *G16H 30/40* | (2018.01) | |
| *G16H 50/20* | (2018.01) | |
| *G06T 7/20* | (2017.01) | |
| *G06T 7/246* | (2017.01) | |
| *A61B 6/02* | (2006.01) | |
| *A61B 90/00* | (2016.01) | |

(52) U.S. Cl.
CPC .............. *A61N 5/1068* (2013.01); *G06T 7/20* (2013.01); *G06T 7/248* (2017.01); *G06T 7/33* (2017.01); *G16H 20/40* (2018.01); *G16H 30/20* (2018.01); *G16H 30/40* (2018.01); *G16H 40/63* (2018.01); *G16H 50/20* (2018.01); *A61B 6/02* (2013.01); *A61B 2090/364* (2016.02); *A61N 5/1084* (2013.01); *A61N 2005/1052* (2013.01); *A61N 2005/1054* (2013.01); *A61N 2005/1055* (2013.01); *A61N 2005/1058* (2013.01); *A61N 2005/1061* (2013.01); *G06T 2200/04* (2013.01); *G06T 2207/10012* (2013.01); *G06T 2207/10081* (2013.01); *G06T 2207/20081* (2013.01); *G06T 2207/20084* (2013.01); *G06T 2207/20108* (2013.01); *G06T 2207/20216* (2013.01); *G06T 2207/30096* (2013.01)

(56) References Cited

U.S. PATENT DOCUMENTS

| | | | |
|---|---|---|---|
| 7,756,567 | B2 | 7/2010 | Kuduvalli et al. |
| 7,894,649 | B2 | 2/2011 | Fu et al. |
| 8,042,209 | B2 | 10/2011 | D'souza et al. |
| 8,086,004 | B2 | 12/2011 | Kuduvalli et al. |
| 8,180,148 | B2 | 5/2012 | Cover et al. |
| 8,249,317 | B2 | 8/2012 | Falen Tony et al. |
| 9,232,928 | B2 | 1/2016 | Mostafavi |
| 9,314,160 | B2 | 4/2016 | Adler, Jr. et al. |
| 9,974,977 | B2 | 5/2018 | Lachaine et al. |
| 10,300,303 | B2 | 5/2019 | Brooks et al. |
| 10,300,305 | B2 | 5/2019 | Lachaine et al. |
| 10,327,666 | B2 | 6/2019 | Lachaine et al. |
| 2008/0021300 | A1 | 1/2008 | Allison |
| 2011/0160566 | A1 | 6/2011 | Petropoulos et al. |
| 2012/0109608 | A1 | 5/2012 | Core et al. |
| 2014/0146936 | A1 | 5/2014 | Liu et al. |
| 2015/0217136 | A1 | 8/2015 | Stanescu et al. |
| 2016/0016007 | A1 | 1/2016 | Bharat et al. |
| 2016/0114192 | A1* | 4/2016 | Lachaine .............. A61N 5/1038 600/1 |
| 2016/0228728 | A1 | 8/2016 | Dempsey et al. |
| 2017/0371001 | A1 | 12/2017 | Dempsey |
| 2018/0192976 | A1 | 7/2018 | Naylor et al. |
| 2018/0193669 | A1 | 7/2018 | Jordan et al. |
| 2019/0038919 | A1 | 2/2019 | Lachaine |
| 2019/0080459 | A1 | 3/2019 | Lachaine |

OTHER PUBLICATIONS

Harris, Wendy, "Accelerating volumetric cine MRI (VC-MRI) using undersampling for real-time 3D target localization tracking in radiation therapy: a feasibility study", Phys. Med. Biol. 63 01NT01, (2018), 12 pgs.

Kluter, Sebastian, "Technical design and concept of a 0.35 T MR-Linac", Clinical and Translational Radiation Oncology 18, (2019), 4 pgs.

Mittauer, Kathryn, "A New Era of Image Guidance with Magnetic Resonance-guided Radiation Therapy for Abdominal and Thoracic Malignancies", Cureus 10(4): e2422. DOI 10.7759 cureus.2422, (Apr. 4, 2018), 12 pgs.

Paganelli, Chiara, "Feasibility study on 3D image reconstruction from 2Dorthogonal cine-MRI for MRI-guided radiotherapy", Journal of Medical Imaging and Radiation Oncology, (2018), 12 pgs.

Saenz, Daniel L, "Characterization of a 0.35T MR system for phantom image quality stability and in vivo assessment of motion quantification", Journal of Applied Clinical Medical Physics, vol. 16, No. 6, (2015), 11 pgs.

Stemkens, Bjorn, "Image-driven, model-based 3D abdominal motion estimation for MR-guided radiotherapy", Physics in Medicine and Biology, Institute of Physics Publishing, Bristol GB, vol. 61, No. 14, XP020306611, [retrieved on Jun. 30, 2016], (Jun. 30, 2016), 5335-5355.

Troels, Bjerre, "Three-dimensional MRI-linac intra-fraction guidance using multiple orthogonal cine-MRI planes", Physics in Medicine and Biology, Institute of Physics Publishing, Bristol GB, vol. 58, No. 14, (Jun. 27, 2013), 4943-4950.

Cho, Seungwook, "Performance enhancement of respiratory tumor motion prediction using adaptive support vector regression: Comparison with adaptive neural network method", International journal of imaging systems and technology 24.1, (2014), 8-15.

"International Application Serial No. PCT/CA2020/050400, International Search Report dated Jul. 2, 2020", 3 pgs.

"International Application Serial No. PCT/CA2020/050400, Written Opinion dated Jul. 2, 2020", 4 pgs.

"International Application Serial No. PCT/CA2020/050401, International Search Report dated Jun. 15, 2020", 5 pgs.

"International Application Serial No. PCT/CA2020/050401, Written Opinion dated Jun. 15, 2020", 5 pgs.

Bertholet, et al., "Real-time intrafraction motion monitoring in external beam radiotherapy", [Online]. Retrieved from the Internet: <https://iopscience.iop.Org/arlicle/10,1088/1361-6560/ab2ba8>, (Feb. 2019).

"U.S. Appl. No. 16/824,234, Non Final Office Action dated Dec. 1, 2020", 17 pgs.

* cited by examiner

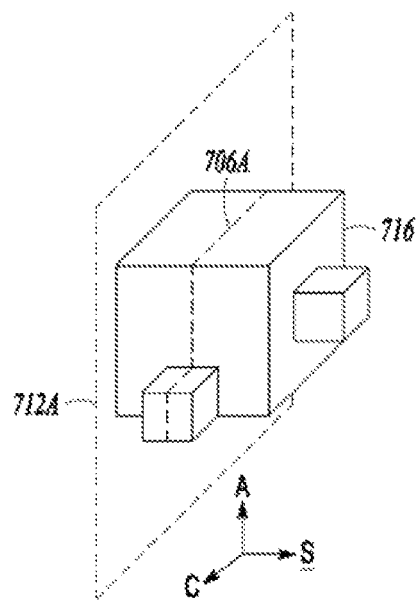
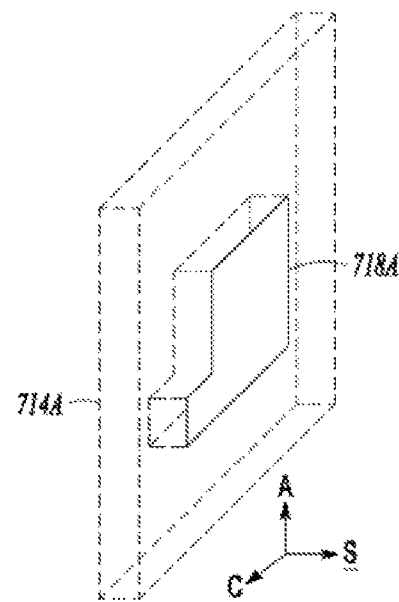
FIG. 7A  FIG. 7B
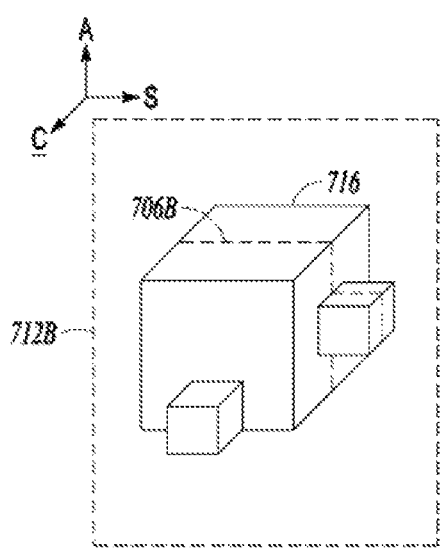
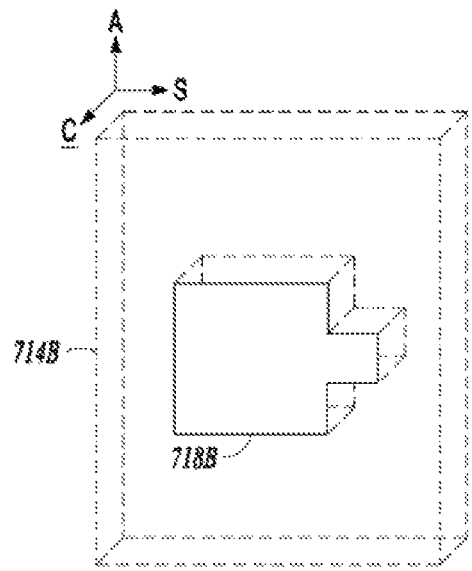
FIG. 7C  FIG. 7D

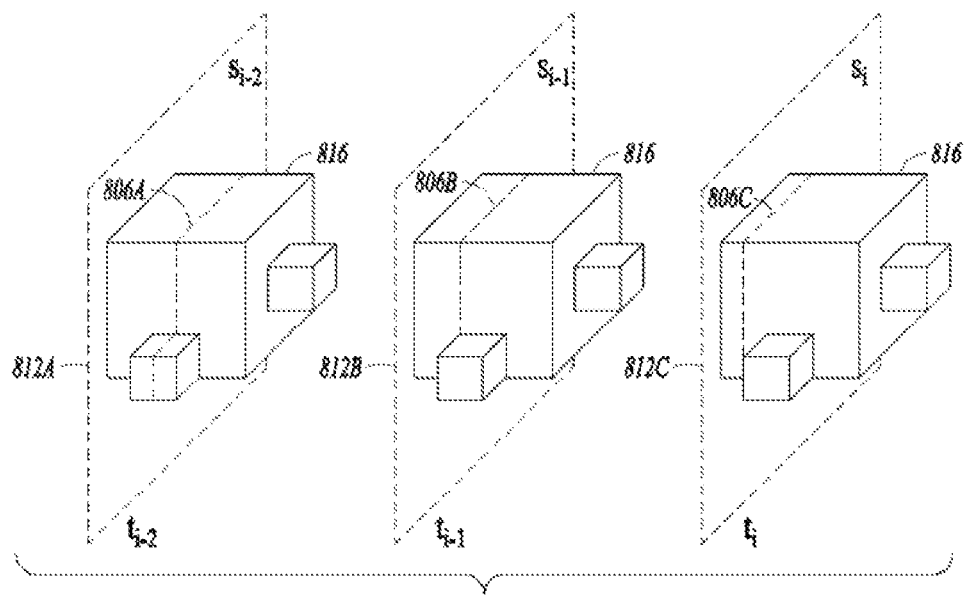
FIG. 8A
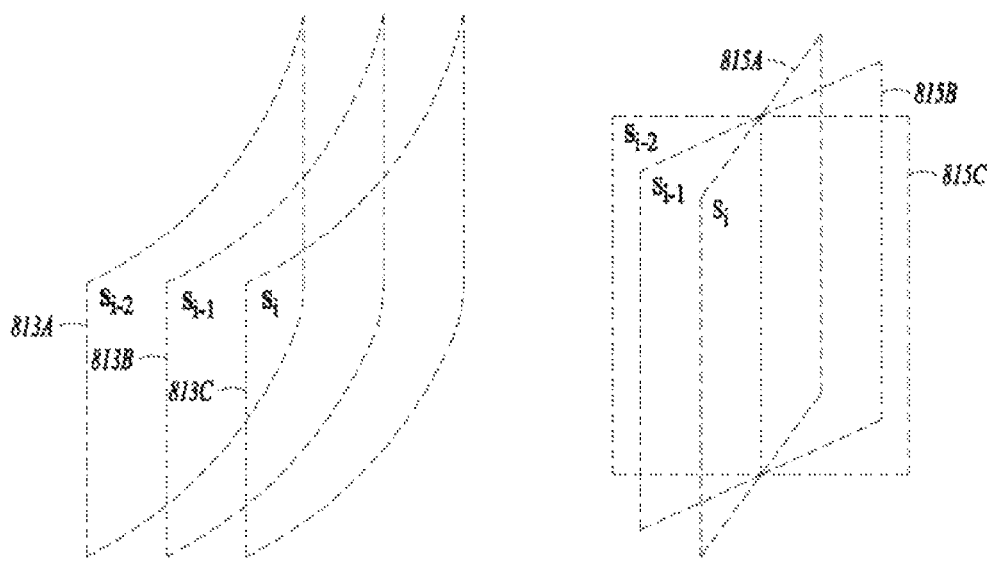
FIG. 8B
FIG. 8C

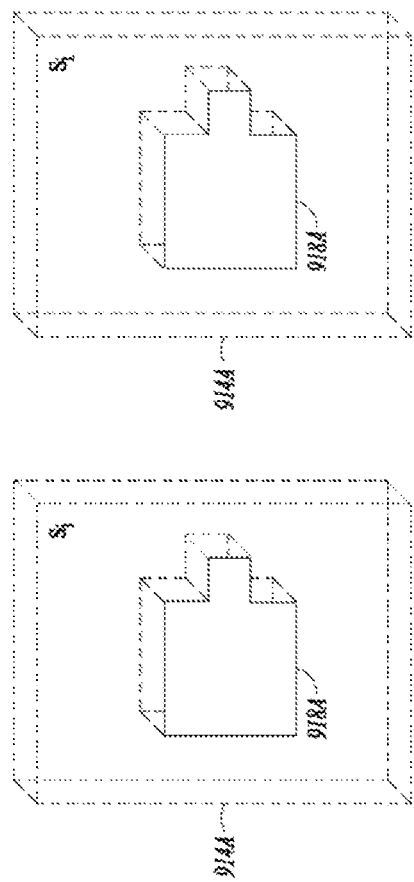
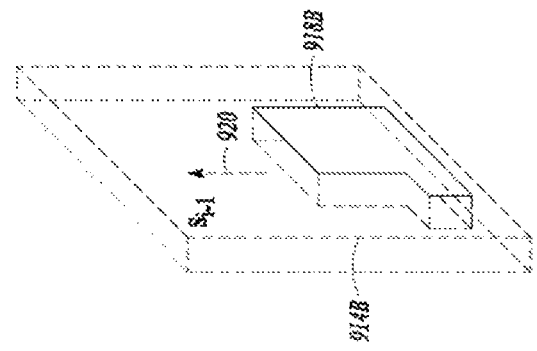
FIG. 9B
FIG. 9A

ADAPTIVE RADIATION THERAPY USING COMPOSITE IMAGING SLICES

CLAIM OF PRIORITY

This patent application claims the benefit of priority of U.S. Provisional Patent Application Ser. No. 62/886,030, titled "AUTOMATIC GATING WITH A MAGNETIC RESONANCE LINEAR ACCELERATOR (MR LINAC)," filed on Aug. 13, 2019, which is hereby incorporated by reference herein in its entirety.

TECHNICAL FIELD

This disclosure generally relates to radiation therapy or radiotherapy. More specifically, the disclosure relates to systems and methods for adapting a radiation therapy treatment plan in order to compensate for changes in a position of a target tumor during the delivery of radiation therapy.

BACKGROUND

Radiation therapy or "radiotherapy" can be used to treat cancers or other ailments in mammalian (e.g., human and animal) tissue. One such radiotherapy technique is a Gamma Knife, by which a patient is irradiated by a large number of low-intensity gamma rays that converge with high intensity and high precision at a target (e.g., a tumor). In another embodiment, radiotherapy is provided using a linear accelerator, whereby a tumor is irradiated by high-energy particles (e.g., electrons, protons, ions, high-energy photons, and the like). The placement and dose of the radiation beam must be accurately controlled to ensure the tumor receives the prescribed radiation, and the placement of the beam should be such as to minimize damage to the surrounding healthy tissue, often called the organ(s) at risk (OARs). Radiation is termed "prescribed" because a physician orders a predefined amount of radiation to the tumor and surrounding organs similar to a prescription for medicine.

Generally, ionizing radiation in the form of a collimated beam is directed from an external radiation source toward a patient.

A specified or selectable beam energy can be used, such as for delivering a diagnostic energy level range or a therapeutic energy level range. Modulation of a radiation beam can be provided by one or more attenuators or collimators (e.g., a multi-leaf collimator). The intensity and shape of the radiation beam can be adjusted by collimation to avoid damaging healthy tissue (e.g., organs at risk) adjacent to the targeted tissue by conforming the projected beam to a profile of the targeted tissue.

The treatment planning procedure may include using a three-dimensional image of the patient to identify a target region (e.g., the tumor) and to identify critical organs near the tumor. Creation of a treatment plan can be a time-consuming process where a planner tries to comply with various treatment objectives or constraints (e.g., dose volume histogram (DVH) objectives), taking into account their individual importance (e.g., weighting) in order to produce a treatment plan that is clinically acceptable. This task can be a time-consuming trial-and-error process that is complicated by the various organs at risk (OARs) because as the number of OARs increases (e.g., up to thirteen for a head-and-neck treatment), so does the complexity of the process. OARs distant from a tumor may be easily spared from radiation, while OARs close to or overlapping a target tumor may be difficult to spare.

Traditionally, for each patient, the initial treatment plan can be generated in an "offline" manner. The treatment plan can be developed well before radiation therapy is delivered, such as using one or more medical imaging techniques. Imaging information can include, for example, images from X-rays, Computed Tomography (CT), nuclear magnetic resonance (MR), positron emission tomography (PET), single-photon emission computed tomography (SPECT), or ultrasound. A health care provider, such as a physician, may use three-dimensional (3D) imaging information indicative of the patient anatomy to identify one or more target tumors along with the organs at risk near the tumor. The health care provider can delineate the target tumor that is to receive a prescribed radiation dose using a manual technique, and the health care provider can similarly delineate nearby tissue, such as organs, at risk of damage from the radiation treatment. Alternatively or additionally, an automated tool (e.g., ABAS provided by Elekta AB, Sweden) can be used to assist in identifying or delineating the target tumor and organs at risk. A radiation therapy treatment plan ("treatment plan") can then be created using an optimization technique based on clinical and dosimetric objectives and constraints (e.g., the maximum, minimum, and mean doses of radiation to the tumor and critical organs).

The treatment plan can then be later executed by positioning the patient and delivering the prescribed radiation therapy. The radiation therapy treatment plan can include dose "fractioning," whereby a sequence of radiation therapy deliveries are provided over a predetermined period of time (e.g., 45 fractions), with each therapy delivery including a specified fraction of a total prescribed dose. However, during treatment the position of the patient and the position of the target tumor in relation to the treatment machine (e.g., linear accelerator—"linac") is very important in order to ensure the target tumor and not healthy tissue is irradiated.

The initial treatment plan can be adapted to the 3D pre-treatment image to compensate for any anatomical changes and set-up differences. During radiation treatment beam-on, additional two-dimensional (2D) cine images can be acquired and used to determine whether to manually pause the beam if the target moves out of tolerance.

Overview

The present inventors have recognized, among other things, that a radiation therapy treatment plan can be adjusted contemporaneously in an adaptive manner in order to compensate for changes in a position of a target tumor during the delivery of radiation therapy to the tumor. For example, a desired target, such as a tumor or other object, can shift in position to such an extent that if an exclusively "offline" approach to therapy planning is used, a location of the tumor indicated by medical images taken prior to treatment can be significantly different from the location of the tumor target during radiation therapy treatment. For example, the tumor may shrink, may move, or can be misaligned compared to the expected or desired location as indicated in the treatment plan. Motion of the target can be caused by one or more sources, such as heart motion, respiration, a reflex such as a cough, or other movements. Therefore, the position of where radiation therapy should be delivered based on images taken prior to treatment can be significantly misaligned with the desired target when the radiation therapy is eventually delivered. In some cases, a "target locus" is a location of the target or object such as prior to treatment, and "a therapy locus" is a location where radiation therapy is delivered during treatment (and ideally is aligned with the actual location of the target at the time of radiation therapy delivery).

In one approach, imaging can be performed contemporaneously with the delivery of a radiation therapy, such as performing an imaging acquisition immediately before initiating radiation therapy delivery during a treatment session, or using a sequence of respective therapy delivery followed by immediately acquiring one or more images of the tumor during a radiation therapy delivery session. Such imaging can provide information helpful for identifying a position of the target or for identifying the motion of the target. Such contemporaneous imaging can be referred to generically as "real-time," but in general a latency or time delay exists between an acquisition of an image and a delivery of radiation therapy, which is generally on the order of about 100 to 500 milliseconds (ms).

Although many cine imaging strategies can be considered, this disclosure focuses on an approach that uses sagittal and coronal 2D images that are centered at or near the target centroid. Other strategies can be adopted, such as using single slices with arbitrary orientation or multiple parallel slices.

A problem exists if an acquisition latency or imaging acquisition rate of three-dimensional volumetric imaging information is unacceptable (e.g., imaging acquisition is too slow to permit therapy guidance or control, such as greater than about 500 ms for respiratory targets). The subject matter described herein can address such a problem, such as by facilitating more rapid acquisition of imaging slices (including one or more of one-dimensional profiles, two-dimensional slices, or three-dimensional volumes comprising a sub-volume or sub-region of an earlier-imaged volumetric region), including comparing information indicative of a portion of the target locus obtained rapidly from one or more imaging slices to information obtained from an earlier-acquired volumetric reference image.

In an example, an adaptive image-guided therapy delivery system can receive imaging information including a volumetric image comprising a target within a radiation therapy patient, and can receive imaging information corresponding to one or more imaging slices comprising different portions of the target, the imaging slices acquired at different instants after acquisition of the volumetric image.

According to various examples, the system receives, at a first time point during the given radiation session, a first imaging slice comprising an object depicted in a 3D pre-treatment volumetric image. The first imaging slice is defined along a first plane (e.g., sagittal plane). At the first time point during the given radiation session, a second imaging slice is accessed comprising the object that was obtained at a second time point that precedes the first time point during the given radiation session. The second imaging slice is defined along a second plane (e.g., coronal plane). The system determines movement of the object at the first time point along first and second directions (e.g., along the sagittal plane and left/right sides) based on the registering the first imaging slice against the volumetric image. Movement of the object along a third direction (e.g., the coronal plane) is determined at the first time point based on the second imaging slice.

In an example, registration between two images finds a transformation that maps one image to the other. In general, a deformable vector field (DVF) maps each point in a first image to a corresponding position in a second image. The first image can be referred to as the fixed image and the second image can be referred to as the moving image. Registrations can be calculated using an optimization technique that tries to find registration values (DVFs) that correspond to an optimum value of a metric. The metric is a quantity that is considered to be representative of the success of the registration. As an optimization iterates closer to the solution, it can use the metric to determine whether each potential step is better or worse than the previous step. In an example, the metric can be the sum of the difference between the moving and the fixed images but can also include more complex metrics such as normalized cross-correlation or mutual information. The optimizer can iterate on improving the registration until the optimum of the metric is found. Other techniques for registration can rely on machine learning. A rigid registration technique can constrain the registration such that the moving image can be mapped to the fixed image by a global translation and rotation or by translation only. If deformations actually exist, the algorithm tries to find the best fit.

In some examples, the system receives, at a first time point during a given radiation session, a first imaging slice comprising an object, the first imaging slice corresponding to a first plane (e.g., the sagittal plane or coronal plane). The system accesses at the first time point a composite imaging slice corresponding to the first plane. The composite imaging slice is generated using a plurality of imaging slices that were obtained prior to the first time point. The first imaging slice is spatially registered with the composite imaging slice to determine movement of the object.

In some examples, the system receives, at a first time point during a given radiation session, a first imaging slice comprising an object, the first imaging slice corresponding to a first plane (e.g., sagittal plane). The system encodes the first imaging slice to a lower dimensional representation and applies a trained machine learning model to the encoded first imaging slice to estimate an encoded version of a second imaging slice corresponding to a second plane (e.g., coronal plane). The first and second imaging slices form a pair of imaging slices for the first time point. The pair of imaging slices are spatially registered to a volumetric image (e.g., a 3D pre-treatment image) to calculate displacement of the object. In some implementations, one or more imaging slices are registered to a volumetric image by inserting the one or more imaging slices (e.g., the pair of imaging slices) into a 3D volume, and filling voxels of the 3D volume where the slices intersect with the voxels. In this way, the registration is a 3D-3D registration but only considering filled voxels of the 3D volume. In another implementation, one or more imaging slices (e.g., the pair of imaging slices) are directly registered to the 3D volume by optimizing a cost function that takes into account how different the slices in the one or more slices are from the volumetric image.

An updated therapy protocol can be generated in an adaptive manner to align the therapy locus established by the therapy beam with an updated target locus or to gate the beam so that the therapy is delivered when the therapy locus passes through the target locus. Updating a therapy protocol can include one or more of (a) adjustment of actuators coupled to a moveable platform such as a couch or table supporting the therapy recipient, (b) adjustment of one or more apertures configured to collimate or shape the therapy beam, (c) adjustment of one or more actuators configured to position a therapy output to establish a specified therapy beam direction, or (d) gating of therapy delivery such as using obtained imaging or information from other sensors, as illustrative examples.

This overview is intended to provide an overview of subject matter of the present patent application. It is not intended to provide an exclusive or exhaustive explanation of the inventive subject matter. The detailed description is included to provide further information about the present patent application.

BRIEF DESCRIPTION OF THE DRAWINGS

FIG. 7A and FIG. 7B illustrate views of an imaging acquisition plane (in FIG. 7A) and a corresponding acquired imaging slice (in FIG. 7B) corresponding to a first imaging plane orientation, according to some embodiments.

FIG. 7C and FIG. 7D illustrate views of an imaging acquisition plane (in FIG. 7C) and a corresponding acquired imaging slice (in FIG. 7D) corresponding to a second imaging plane orientation, such as can be orthogonal to the first imaging plane orientation mentioned above in relation to FIG. 7A and FIG. 7B, according to some embodiments.

FIG. 8A illustrates generally a series of imaging acquisition planes, such as can be obtained as a target locus moves from one imaging acquisition instance to another, according to some embodiments.

FIG. 8B illustrates generally a series of imaging acquisition regions, such as can include a curved shape, according to some embodiments.

FIG. 8C illustrates generally a series of imaging acquisition planes, such as can include different orientations that need not each be orthogonal to the others, according to some embodiments.

FIG. 9A illustrates generally a series of two imaging slices, such as including a target locus that is displaced between first and second imaging slices, according to some embodiments.

FIG. 9B illustrates generally a series of two spatially-registered imaging slices, such as after a segmented portion of the target locus is adjusted in one or more of the imaging slices, according to some embodiments.

Figure 1A:
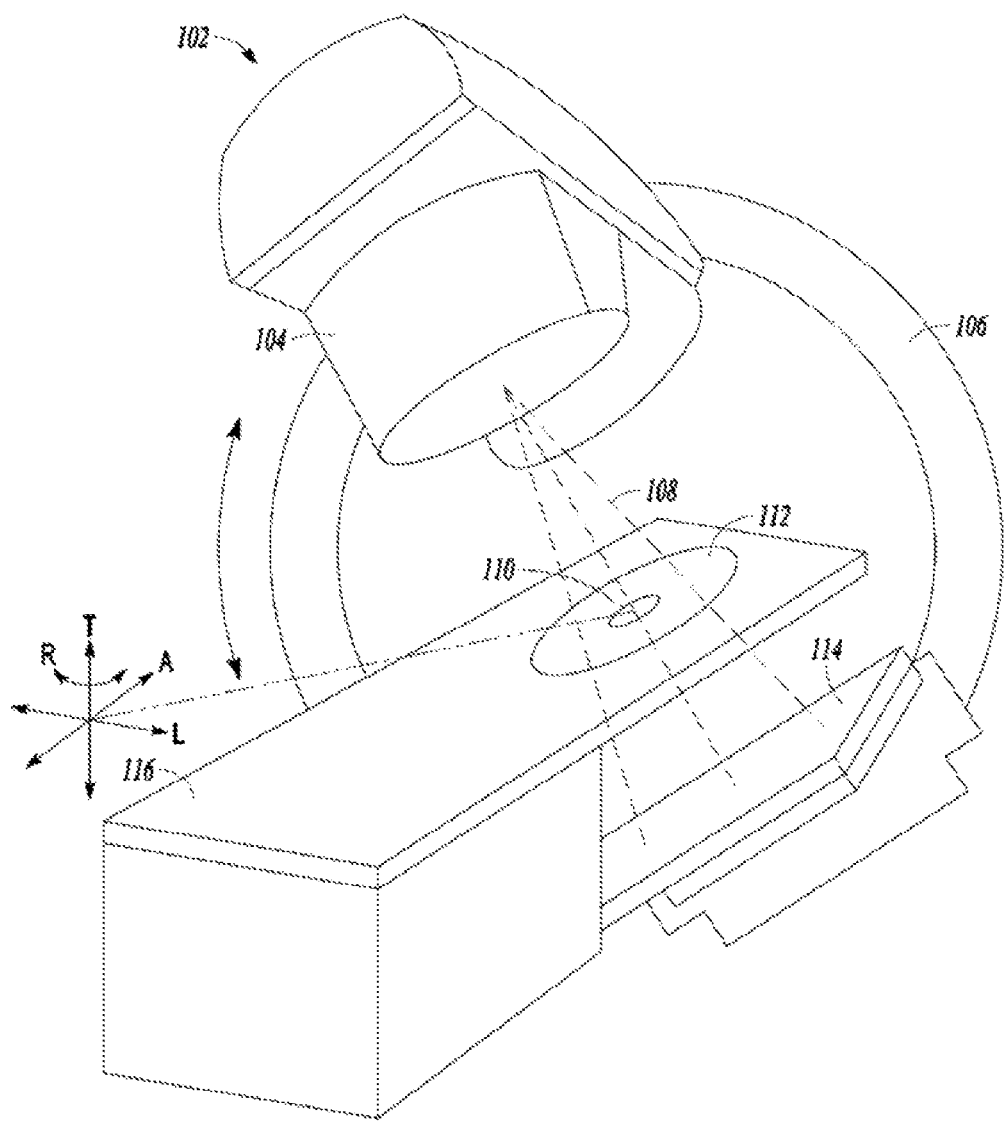
FIG. 1A illustrates generally an example of a radiation therapy system that can include radiation therapy output configured to provide a therapy beam, according to some embodiments.

In the drawings, which are not necessarily drawn to scale, like numerals may describe similar components in different views. Like numerals having different letter suffixes may represent different instances of similar components. The drawings illustrate generally, by way of example, but not by way of limitation, various embodiments discussed in the present document.

DETAILED DESCRIPTION

FIG. 1A illustrates generally an example of a radiation therapy system 102 that can include radiation therapy output 104 configured to provide a therapy beam 108. The radiation therapy output 104 can include one or more attenuators or collimators, such as a multi-leaf collimator (MLC) as described in the illustrative example of FIG. 4. Referring back to FIG. 1A, a patient can be positioned in a region 112, such as on a platform 116 (e.g., a table or a couch), to receive a radiation therapy dose according to a radiation therapy treatment plan. The radiation therapy output 104 can be located on a gantry 106 or other mechanical support, such as to rotate the therapy output 104 around an axis ("A"). One or more of the platform 116 or the radiation therapy output 104 can be moveable to other locations, such as moveable in transverse direction ("T") or a lateral direction ("L"). Other degrees of freedom are possible, such as rotation about one or more other axes, such as rotation about a transverse axis (indicated as "R").

The coordinate system (including axes A, T, and L) shown in FIG. 1A can have an origin located at an isocenter 110. The isocenter 110 can be defined as a location where the radiation therapy beam 108 intersects the origin of a coordinate axis, such as to deliver a prescribed radiation dose to a location on or within a patient. For example, the isocenter 110 can be defined as a location where the radiation therapy beam 108 intersects the patient for various rotational positions of the radiation therapy output 104 as positioned by the gantry 106 around the axis A.

In an example, a detector 114 can be located within a field of the therapy beam 108, such as can include a flat panel detector (e.g., a direct detector or a scintillation-based detector). The detector 114 can be mounted on the gantry 106 opposite the radiation therapy output 104, such as to maintain alignment with the therapy beam 108 as the gantry 106 rotates. In this manner, the detector 114 can be used to monitor the therapy beam 108 or the detector 114 can be used for imaging, such as portal imaging.

In an illustrative example, one or more of the platform 116, the therapy output 104, or the gantry 106 can be automatically positioned, and the therapy output 104 can establish the therapy beam 108 according to a specified dose for a particular therapy delivery instance. A sequence of therapy deliveries can be specified according to a radiation therapy treatment plan, such as using one or more different orientations or locations of the gantry 106, platform 116, or therapy output 104. The therapy deliveries can occur sequentially, but can intersect in a desired therapy locus on or within the patient, such as at the isocenter 110. A prescribed cumulative dose of radiation therapy can thereby be delivered to the therapy locus while damage to tissue nearby the therapy locus is reduced or avoided.

As mentioned in relation to other examples herein, the radiation therapy system 102 can include or can be coupled to an imaging acquisition system, such as to provide one or more of nuclear magnetic resonance (MR) imaging, X-ray imaging, such as can include computed tomography (CT) imaging, or ultrasound imaging. In an example, MR imaging information or other imaging information can be used to generate imaging information or visualizations equivalent to CT imaging, without requiring actual CT imaging. Such imaging can be referred to as "pseudo-CT" imaging.

Figure 1B:
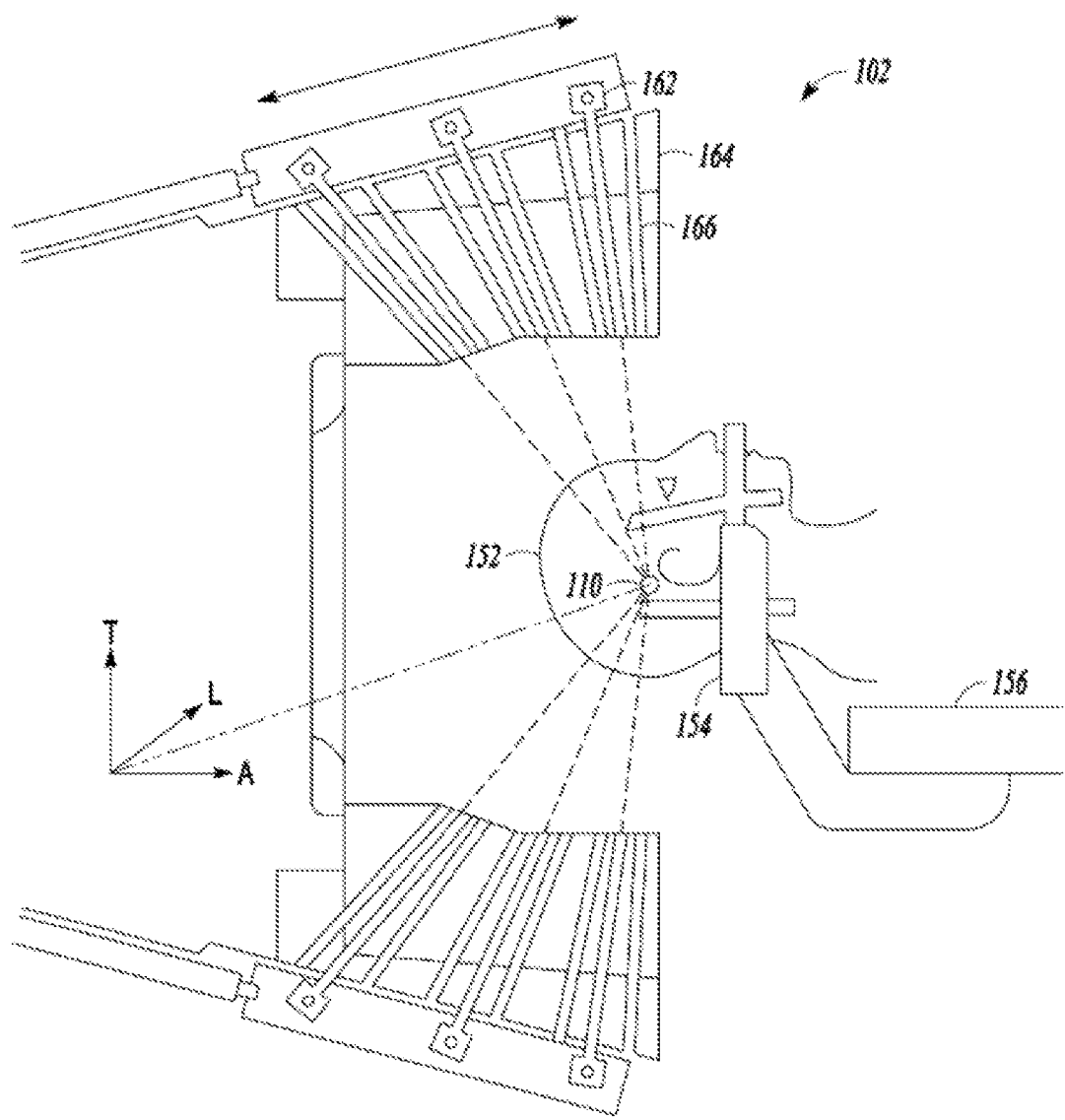
FIG. 1B illustrates generally another example of a radiation therapy system, according to some embodiments.

FIG. 1B illustrates generally another example of a radiation therapy system 102 (e.g., Leksell Gamma Knife manufactured by Elekta, AB, Stockholm, Sweden), according to some embodiments of the present disclosure. As shown in FIG. 1B, in a radiation therapy treatment session, a patient 152 may wear a coordinate frame 154 to stabilize a portion of the patient's anatomy (e.g., the head) undergoing surgery or radiation therapy. Coordinate frame 154 and a patient positioning system 156 may establish a spatial coordinate system, which may be used while imaging a patient or during radiation surgery.

Radiation therapy system 102 may include a protective housing 164 to enclose a plurality of radiation sources 162. Radiation sources 162 may generate a plurality of radiation beams (e.g., beamlets) through beam channels 166. The plurality of radiation beams may be configured to focus on an isocenter 110 from different directions. While each individual radiation beam may have a relatively low intensity, isocenter 110 may receive a relatively high level of radiation when multiple doses from different radiation beams accumulate at isocenter 110. In certain embodiments, isocenter 110 may correspond to a target under surgery or treatment, such as a tumor.

Figure 2:
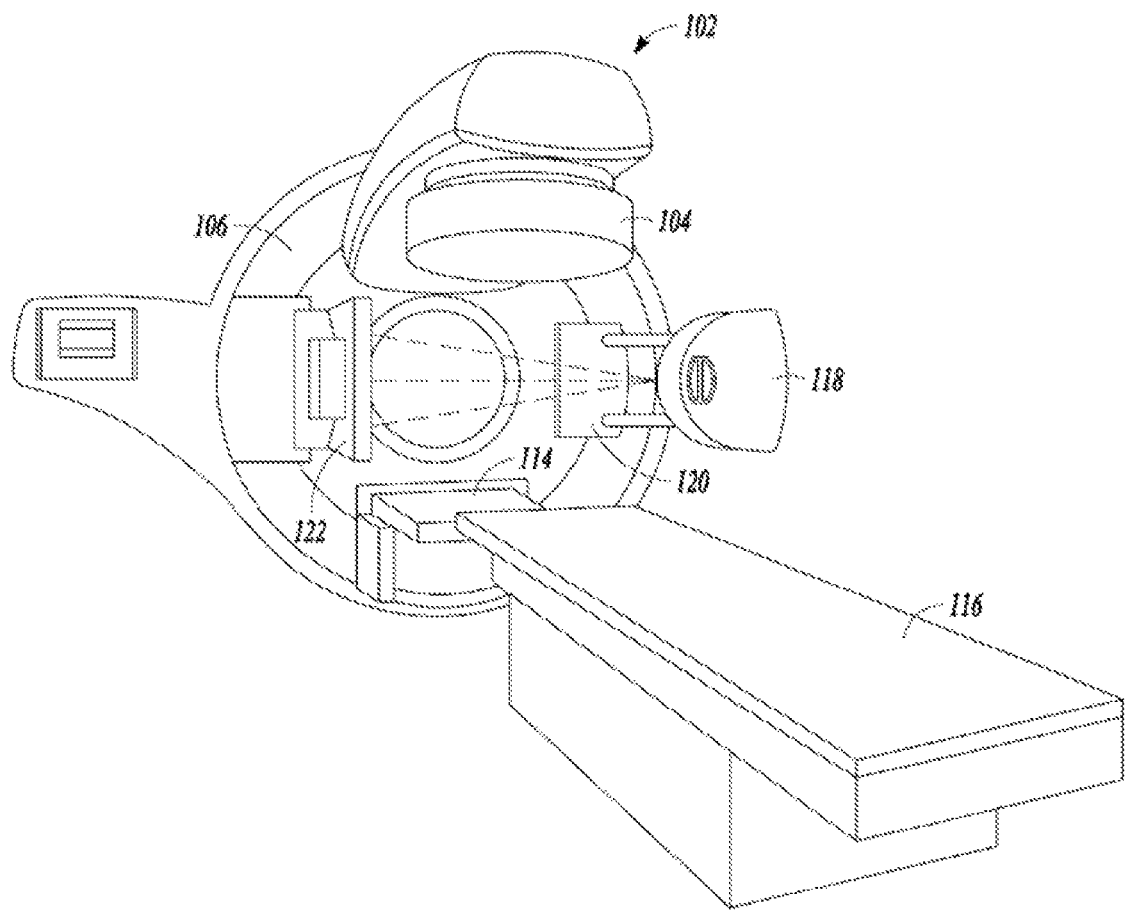
FIG. 2 illustrates generally an example of a system that can include a combined radiation therapy system and an imaging system, such as can include a computed tomography (CT) imaging system, according to some embodiments.

FIG. 2 illustrates generally an example of a system that can include a combined radiation therapy system 102 and an imaging system, such as can include a computed tomography (CT) imaging system. The CT imaging system can include an imaging X-ray source 118, such as providing X-ray energy in a kiloelectron-Volt (keV) energy range. The imaging X-ray source 118 provides one or more of fan-shaped or conical beam 120 directed to an imaging detector 122, such as a flat panel detector. The radiation therapy system 102 can be similar to the system 102 described in relation to FIG. 1A, such as including a radiation therapy output 104, a gantry 106, a platform 116, and another flat panel detector 114. As in the examples of FIG. 1A, FIG. 1B, and FIG. 3, the radiation therapy system 102 can be coupled to, or can include, a high-energy accelerator configured to provide a therapeutic radiation beam. The X-ray source 118 can provide a comparatively-lower-energy X-ray diagnostic beam, for imaging.

In the illustrative example of FIG. 2, the radiation therapy output 104 and the X-ray source 118 can be mounted on the same rotating gantry 106, rotationally-separated from each other by 90 degrees. In another example, two or more X-ray sources can be mounted along the circumference of the gantry 106, such as each having its own detector arrangement to provide multiple angles of diagnostic imaging concurrently. Similarly, multiple radiation therapy outputs 104 can be provided.

Figure 3:
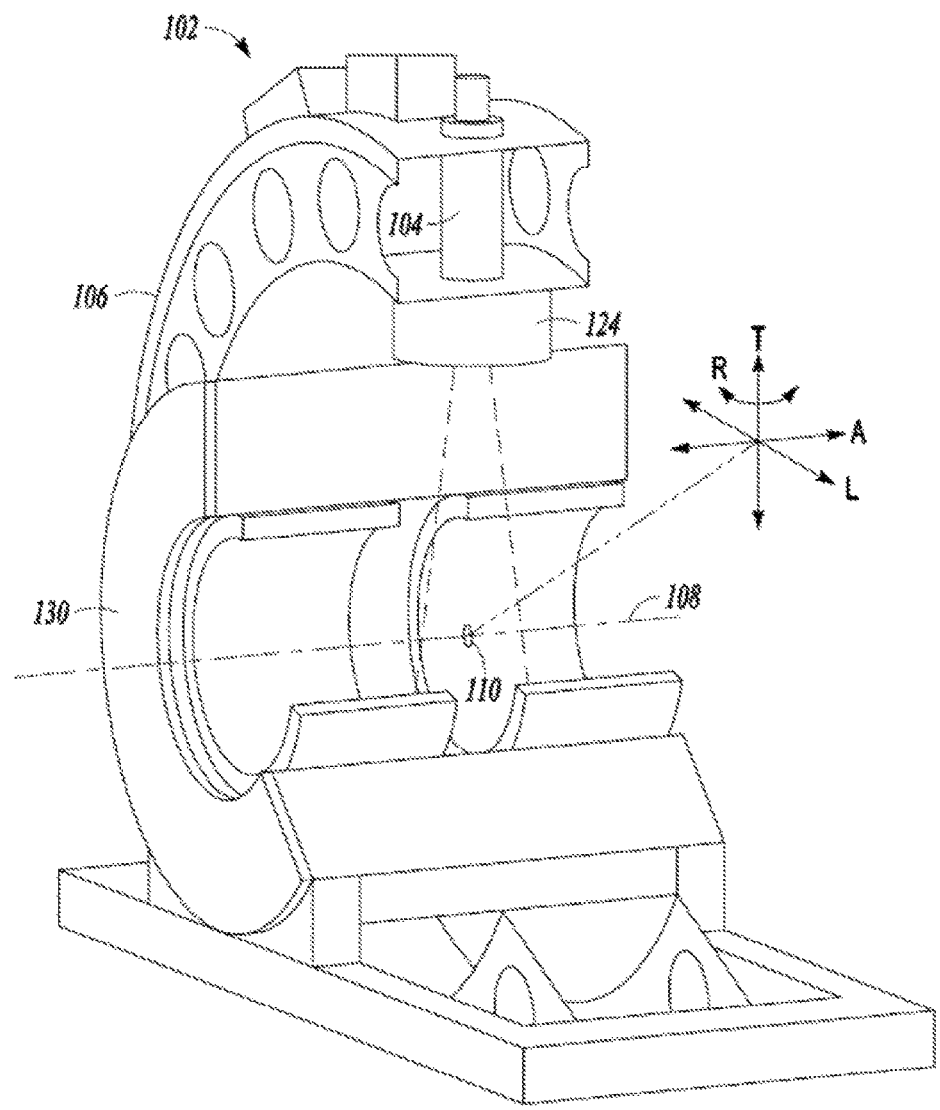
FIG. 3 illustrates generally a partially cut-away view of an example of a system that can include a combined radiation therapy system and an imaging system, such as can include a nuclear magnetic resonance (MR) imaging system, according to some embodiments.

FIG. 3 illustrates generally a partially cut-away view of an example of a system that can include a combined radiation therapy system 102 and an imaging system, such as can include a nuclear magnetic resonance (MR) imaging system 130. The MR imaging system 130 can be arranged to define a "bore" around an axis ("A"), and the radiation therapy system can include a radiation therapy output 104, such as to provide a radiation therapy beam 108 directed to an isocenter 110 within the bore along the axis, A. The radiation therapy output 104 can include a collimator 124, such as to one or more of control, shape, or modulate radiation therapy beam 108 to direct the beam 108 to a therapy locus aligned with a desired target locus within a patient. The patient can be supported by a platform, such as a platform positionable along one or more of an axial direction, A, a lateral direction, L, or a transverse direction, T. One or more portions of the radiation therapy system 102 can be mounted on a gantry 106, such as to rotate the radiation therapy output 104 about the axis A.

FIG. 1A, FIG. 1B, FIG. 2, and FIG. 3 illustrate generally examples including a configuration where a therapy output can be rotated around a central axis (e.g., an axis "A"). Other radiation therapy output configurations can be used. For example, a radiation therapy output can be mounted on a robotic arm or manipulator, such as having multiple degrees of freedom. In yet another example, the therapy output can be fixed, such as located in a region laterally separated from the patient, and a platform supporting the patient can be used to align a radiation therapy isocenter with a specified target locus within the patient.

Figure 4:
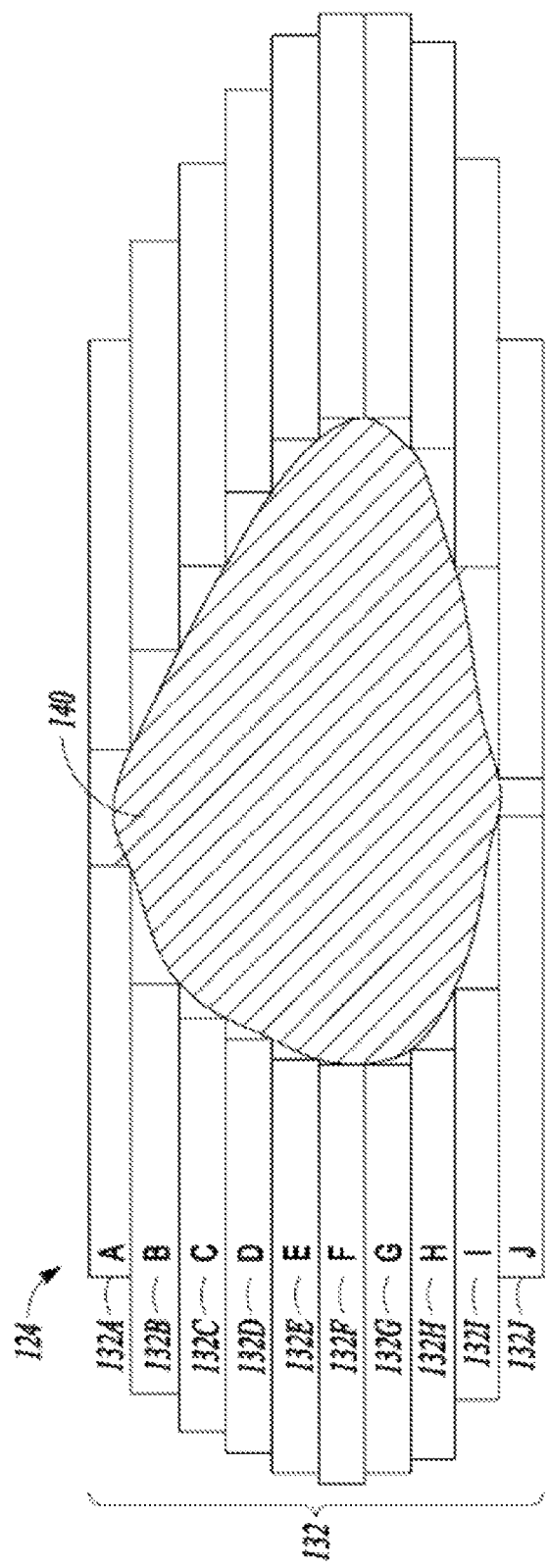
FIG. 4 illustrates generally an example of a collimator configuration, such as can be used to one or more of shape, direct, or modulate an intensity of a radiation therapy beam, according to some embodiments.

FIG. 4 illustrates generally an example of a multi-leaf collimator (MLC) 132, such as can be used to one or more of shape, direct, or modulate an intensity of a radiation therapy beam. In FIG. 4, leaves 132A through 132J can be automatically positioned to define an aperture approximating a tumor 140 cross-section or projection. The leaves 132A through 132J can be made of a material specified to attenuate or block the radiation beam in regions other than the aperture, in accordance with the radiation treatment plan. For example, the leaves 132A through 132J can include metallic plates, such as comprising tungsten, with a long axis of the plates oriented perpendicular to a beam direction, and having ends oriented parallel to the beam direction (as shown in the plane of the illustration of FIG. 4). A "state" of the MLC 132 can be adjusted adaptively during a course of radiation therapy, such as to establish a therapy beam that better approximates a shape or location of the tumor 140 or other target locus, as compared to using a static collimator configuration or as compared to using an MLC 132 configuration determined exclusively using an "offline" therapy planning technique. A radiation therapy technique including using the MLC 132 to produce a specified radiation dose distribution to a tumor or to specific areas within a tumor can be referred to as Intensity Modulated Radiation Therapy (IMRT).

Figure 5:
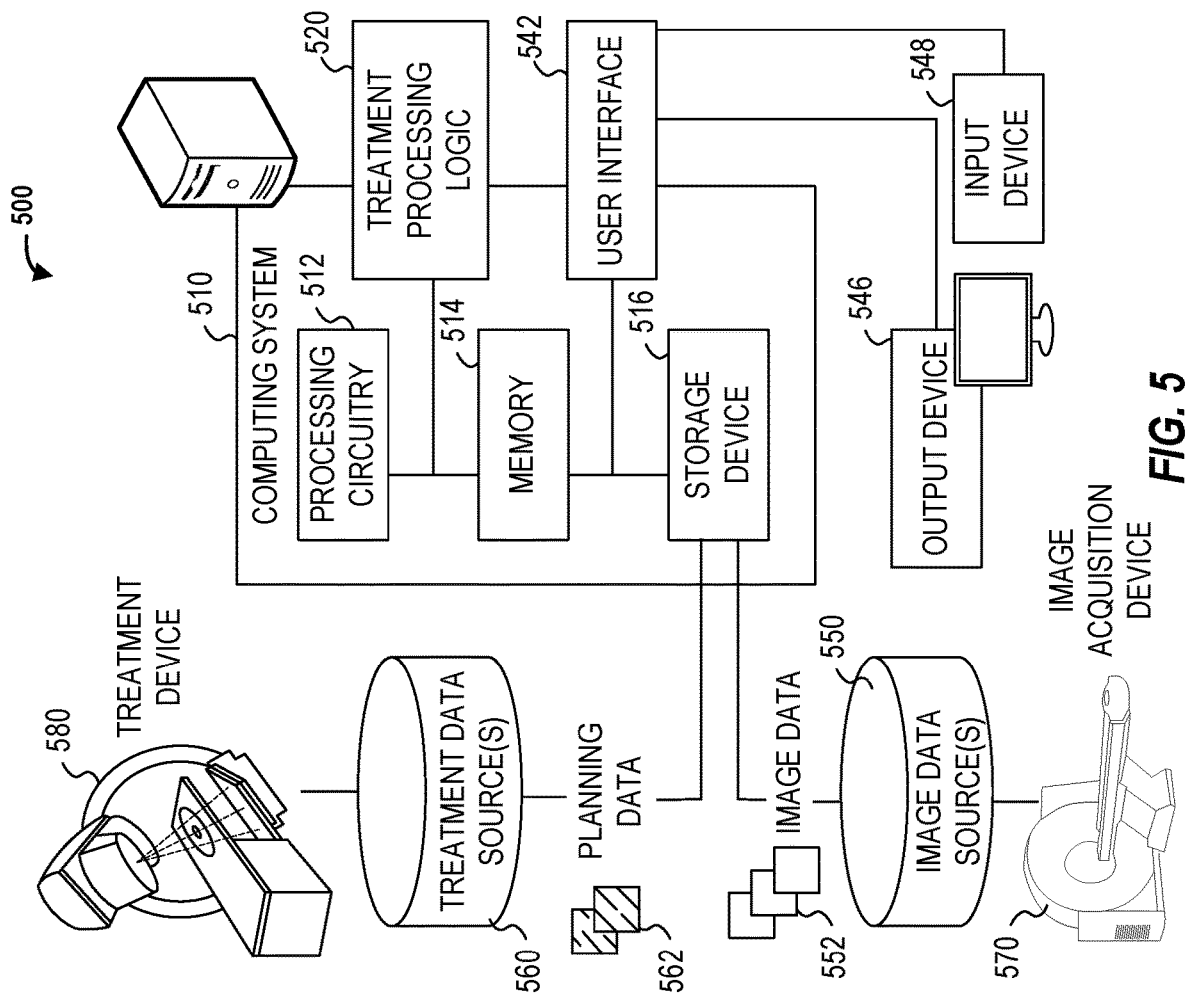
FIG. 5 illustrates generally an example of a radiation therapy system, such as can include a radiation therapy device and an imaging acquisition device, according to some embodiments.

FIG. 5 illustrates an exemplary radiotherapy system 500 adapted to perform radiotherapy plan processing operations using one or more of the approaches discussed herein. These radiotherapy plan processing operations are performed to enable the radiotherapy system 500 to provide radiation therapy to a patient based on specific aspects of captured medical imaging data and therapy dose calculations or radiotherapy machine configuration parameters.

The radiotherapy system 500 includes a radiotherapy processing computing system 510 which hosts treatment processing logic 520. Specifically, treatment processing logic 520 implements various techniques discussed in relation to FIGS. 12-19 to detect object movement during real-time delivery of a radiotherapy session and to update a therapy protocol. It will be understood, however, that many variations and use cases of the following treatment processing logic 520 may be provided, including in data verification, visualization, and other medical evaluative and diagnostic settings. The radiotherapy processing computing system 510 may be connected to a network (not shown), and such network may be connected to the Internet. For instance, a network can connect the radiotherapy processing computing system 510 with one or more medical information sources (e.g., a radiology information system (RIS), a medical record system (e.g., an electronic medical record (EMR)/ electronic health record (EHR) system), an oncology information system (OIS)), one or more image data sources 550, an image acquisition device 570 (e.g., an imaging modality), a treatment device 580 (e.g., a radiation therapy device, also referred to herein as a radiotherapy device), and treatment data source(s) 560.

As an example, the radiotherapy processing computing system 510 can be configured to receive, at a first time point during the given radiation session, a first imaging slice comprising an object depicted in a 3D pre-treatment volumetric image. The first imaging slice is defined along a first plane (e.g., sagittal plane). At the first time point during the given radiation session, a second imaging slice is accessed comprising the object that was obtained at a second time point that precedes the first time point during the given radiation session. The second imaging slice is defined along a second plane (e.g., coronal plane). The system determines movement of the object at the first time point along first and second directions (e.g., along the sagittal plane and left/right sides) based on the registering the first imaging slice against the volumetric image. Movement of the object along a third direction (e.g., the coronal plane) is determined at the first time point based on the second imaging slice.

Specifically, the radiotherapy processing computing system 510 can determine movement of an object according to a second technique, during a radiotherapy treatment session, along three directions (e.g., sagittal, coronal, and left/right planes). It does so by registering an image (e.g., a cine image) received along one plane (e.g., the sagittal plane), at a particular point in the treatment session, with a pre-treatment 3D volumetric image. The result provides movement of the object along the sagittal plane and the left/right plane. At the same particular point, the radiotherapy processing computing system 510 retrieves a previously obtained image (e.g., a cine image) along the other plane (e.g., the coronal plane). The radiotherapy processing computing system 510 uses the position of the object in the previously obtained image slice to determine movement of the object along the coronal plane. As a result, movement of the object can be determined at a given time point in the treatment session along three directions (e.g., 3D movement of the object can be determined). For example, the first direction corresponds to an anterior/posterior direction, the second direction corresponds to a superior/inferior direction, and the third direction corresponds to a left/right direction. The object can include at least one of an anatomy portion of a patient, a pixel, or any defined image portion. The first and second imaging slices are planar or orthogonal but can be any two imaging slices along any other parallel or perpendicular direction.

In some cases, in order to determine movement of the object along the current plane direction (e.g., the direction corresponding to the image that is currently obtained rather than the previously obtained image), the radiotherapy processing computing system 510 extracts, from the volumetric image, a first two-dimensional (2D) slice along the first plane. The radiotherapy processing computing system 510 spatially registers the first imaging slice and the first 2D slice (e.g., by moving a portion of the object in the first imaging slice to register the object in the first imaging slice with a portion of the object in the first 2D slice.

In some embodiments, the radiotherapy processing computing system 510 registers the second imaging slice (corresponding to an earlier time point in the treatment session) against the pre-treatment image to determine movement along the third direction. In such cases, the radiotherapy processing computing system 510 defines the first and second imaging slices (defined along respective first and second planes) as moving images and the 2D slice is extracted from the volumetric pre-treatment image as the fixed image to perform 2D/2D image registration. The radiotherapy processing computing system 510 then determines movement along the three directions based on the registered first and second image slices with the 3D pre-treatment volumetric image.

In some embodiments, radiotherapy processing computing system 510 computes in-plane shifts of the object along the first and second directions based on the first imaging slice and the first 2D slice. The radiotherapy processing computing system 510 computes an out-of-plane shift value along the third direction based on the second imaging slice. For example, the radiotherapy processing computing system 510 computes in-plane shifts of the object along the sagittal direction and the left/right direction based on the first imaging slice that is defined along the sagittal direction and the first 2D slice extracted from the pre-treatment volumetric image. The radiotherapy processing computing system 510 computes an out-of-plane shift value along the coronal direction based on the second imaging slice that is defined along the coronal direction.

In some cases, the radiotherapy processing computing system 510 predicts a difference between the second imaging slice defined along the second plane and an expected imaging slice defined along the second plane at the first time point. For example, the radiotherapy processing computing system 510 applies a machine learning technique to the second imaging slice (obtained at a prior point in time) to predict or estimate the second imaging slice at the current point in time in the radiotherapy session. The predicted or estimated second imaging slice defined along the second plane can then be used in conjunction with the first imaging slice defined along the first plane to determine movement of the object along three directions at the current time point.

In some embodiments, the radiotherapy processing computing system 510 determines a metric indicative of an alignment between a portion of the object from the first imaging slice and a portion of the object from the first 2D slice. The radiotherapy processing computing system 510 adjusts a position of the second imaging slice to improve an alignment between the portion of the object from the first imaging slice and the portion of the object from the first 2D slice. In some cases, the metric is determined by masking a portion of the first imaging slice and a slice of the volumetric image. In some cases, the metric is determined by determining a similarity between a line of intersection between the portion of the object from the first imaging slice and the portion of the object from a slice of the volumetric image.

In some embodiments, the radiotherapy processing computing system 510 determines movement during a radiotherapy treatment session according to a third technique. For example, the radiotherapy processing computing system 510 receives, at a first time point during a given radiation session, a first imaging slice comprising an object. The first imaging slice may correspond to a first plane (e.g., the sagittal plane). The radiotherapy processing computing system 510 accesses, at the first time point during the given radiation session, a composite imaging slice corresponding to the first plane. The composite imaging slice is generated using a plurality of imaging slices that were obtained prior to the first time point. The radiotherapy processing computing system 510 spatially registers the first imaging slice and the composite imaging slice to determine movement of the object. The radiotherapy processing computing system 510 generates an updated therapy protocol to control delivery of a therapy beam based on the determined movement.

In some cases, the radiotherapy processing computing system 510 registers the first imaging slice and the composite imaging slice by mask limiting pixels considered in the registration in one or both of the first imaging slice and the composite imaging slice. The composite imaging slice is registered to the two-dimensional slice extracted from the volumetric image before the first imaging slice is registered to the composite imaging slice. In some cases, the composite image that is registered to the two-dimensional slice extracted from the volumetric image is manually adjusted by a user input to specify or change a position or portion of the composite image that is registered relative to the two-dimensional slice.

In some embodiments, the composite image is a first composite image. At a second time point during the given radiation session, the radiotherapy processing computing system 510 receives a second imaging slice that corresponds to a second plane (e.g., a coronal plane). The radiotherapy processing computing system 510 accesses, at the second time point during the given radiation session, a second composite imaging slice corresponding to the second plane. The second composite imaging slice is generated using another plurality of imaging slices obtained prior to the second time point. The radiotherapy processing computing system 510 spatially registers the second imaging slice and the second composite imaging slice, including moving a portion of the object in the second imaging slice to register the object in the second imaging slice with a portion of the object in the second composite imaging slice.

In some embodiments, the composite image is generated by averaging a selected subset of imaging slices. For example, a plurality of imaging slices are obtained prior to activating the radiotherapy beam during the given radiation session. A given one of the slices that corresponds to a reference breathing phase is selected as a target image. The radiotherapy processing computing system 510 deformably registers a remaining set of the plurality of imaging slices to the selected target image. The radiotherapy processing computing system 510 averages the deformably registered plurality of imaging slices and determines an average offset for each of the plurality of imaging slices. The radiotherapy processing computing system 510 resamples the imaging slices based on the average offset to select a subset of the resampled imaging slices based on a distance of each of the resampled imaging slices to the target image (e.g., the selected imaging slice). For example, the radiotherapy processing computing system 510 selects those imaging slices for which the distances between the slices and the target slice is less than a specified threshold. The composite image is then generated by averaging the selected subset of the resampled plurality of imaging slices.

In some embodiments, the radiotherapy processing computing system 510 determines movement during a radiotherapy treatment session according to a fourth technique. For example, the radiotherapy processing computing system 510 receives, at a first time point in a given radiation session, a first imaging slice corresponding to a first plane (e.g., a 2D cine image corresponding to or defined along a sagittal plane). The radiotherapy processing computing system 510 encodes the first imaging slice to a lower dimensional representation (e.g., by converting principal component analysis (PCA) components of a deformable vector field (DVF) of the first imaging slice to estimate the PCA components of the second imaging slice). In one example, the encoding the slices to lower dimensional representation includes reducing the amount of data used to represent a given slice by converting the standard used to represent the slice from one standard to another. The radiotherapy processing computing system 510 applies a trained machine learning model (e.g., a support vector machine or random forest machine or neural network) to the encoded first imaging slice to estimate an encoded version of a second imaging slice corresponding to a second plane (e.g., the coronal plane) at the first time point to provide a pair of imaging slices for the first time point. The radiotherapy processing computing system 510 simultaneously spatially registers the pair of imaging slices to a volumetric image (e.g., a 3D pre-treatment volume of the patient), received prior to the given radiation session, comprising a time-varying object to calculate displacement of the object. The radiotherapy processing computing system 510 generates an updated therapy protocol to control delivery of a therapy beam based on the calculated displacement of the object. In some cases, prior to registering the images, the radiotherapy processing computing system 510 decodes the estimated encoded version of the second imaging slice to obtain the second imaging slice at the first time point. For example, the radiotherapy processing computing system 510 converts or upscales the data used to represent the imaging slice from one standard to another. In order to encode and decode the slices, according to the disclosed techniques, any suitable compression and decompression algorithm can be used.

In some cases, the pair of imaging slices include a stereo pair of imaging slices, such that the first plane is orthogonal to the second plane or the first plane is tilted (e.g., non-orthogonal) relative to the second plane. In some cases, to train the machine learning model to perform the prediction in the fourth technique, the radiotherapy processing computing system 510 receives, prior to the given radiation session, a first sequence of training imaging slices corresponding to the first plane. The radiotherapy processing computing system 510 also receives, prior to the given radiation session, a second sequence of training imaging slices corresponding to the second plane. The second sequence of training imaging slices can be received concurrently with or alternatively with the first sequence of imaging slices. The radiotherapy processing computing system 510 encodes the first and second sequences to a lower dimensional representation (e.g., converts the data used to represent the first and second sequences from one standard to another to reduce the amount of data used to represent the sequences). In some implementations, the radiotherapy processing computing system 510 interpolates a first training image slice of the first sequence of training imaging slices corresponding to a first training time point to generate a first interpolated training imaging slice corresponding to a second training time point when a second training image slice of the second sequence of training imaging slices is received at the second training time point. Specifically, the radiotherapy processing computing system 510 interpolates or generates an expected version of the first training image slice for a next adjacent time point that corresponds to the time point at which one of the training imaging slices of the second plane is received. The radiotherapy processing computing system 510 trains the machine learning model based on the interpolated image to predict a first image corresponding to the first plane from a second image corresponding to the second plane. The radiotherapy processing computing system 510 continuously or periodically trains the machine learning model during the given radiation session as new imaging slices are captured and received.

The radiotherapy processing computing system 510 may include processing circuitry 512, memory 514, a storage device 516, and other hardware and software-operable features such as a user interface 542, a communication interface (not shown), and the like. The storage device 516 may store transitory or non-transitory computer-executable instructions, such as an operating system, radiation therapy treatment plans (e.g., training data, treatment planning strategies, patient movement models, patient deformation models, beam delivery segment information, 5D and/or 2D image information for a patient, and device adjustment parameters, and the like), software programs (e.g., image processing software, image or anatomical visualization software, etc.), and any other computer-executable instructions to be executed by the processing circuitry 512.

In an example, the processing circuitry 512 may include a processing device, such as one or more general-purpose processing devices such as a microprocessor, a central processing unit (CPU), a graphics processing unit (GPU), an accelerated processing unit (APU), or the like. More particularly, the processing circuitry 512 may be a complex instruction set computing (CISC) microprocessor, a reduced instruction set computing (RISC) microprocessor, a very long instruction Word (VLIW) microprocessor, a processor implementing other instruction sets, or processors implementing a combination of instruction sets. The processing circuitry 512 may also be implemented by one or more special-purpose processing devices such as an application-specific integrated circuit (ASIC), a field programmable gate array (FPGA), a digital signal processor (DSP), a System on a Chip (SoC), or the like.

As would be appreciated by those skilled in the art, in some examples, the processing circuitry 512 may be a special-purpose processor, rather than a general-purpose processor. The processing circuitry 512 may include one or more known processing devices, such as a microprocessor from the Pentium™, Core™, Xeon™ or Itanium® family manufactured by Intel™, the Turion™, Athlon™, Sempron™ Opteron™, FX™, Phenom™ family manufactured by AMD™, or any of various processors manufactured by Sun Microsystems. The processing circuitry 512 may also include graphical processing units such as a GPU from the GeForce®, Quadro®, Tesla® family manufactured by Nvidia™, GMA, Iris™ family manufactured by Intel™, or the Radeon™ family manufactured by AMD™. The processing circuitry 512 may also include accelerated processing units such as the Xeon Phi™ family manufactured by Intel™. The disclosed embodiments are not limited to any type of processor(s) otherwise configured to meet the computing demands of identifying, analyzing, maintaining, generating, and/or providing large amounts of data or manipulating such data to perform the methods disclosed herein. In addition, the term "processor" may include more than one physical (circuitry based) or software-based processor, for example, a multi-core design or a plurality of processors each having a multi-core design. The processing circuitry 512 can execute sequences of transitory or non-transitory computer program instructions, stored in memory 514, and accessed from the storage device 516, to perform various operations, processes, methods that will be explained in greater detail below. It should be understood that any component in radiotherapy system 500 may be implemented separately and operate as an independent device and may be coupled to any other component in radiotherapy system 500 to perform the techniques described in this disclosure.

The memory 514 may comprise read-only memory (ROM), a phase-change random access memory (PRAM), a static random access memory (SRAM), a flash memory, a random access memory (RAM), a dynamic random access memory (DRAM) such as synchronous DRAM (SDRAM), an electrically erasable programmable read-only memory (EEPROM), a static memory (e.g., flash memory, flash disk, static random access memory) as well as other types of random access memories, a cache, a register, a compact disc read-only memory (CD-ROM), a digital versatile disc (DVD) or other optical storage, a cassette tape, other magnetic storage device, or any other non-transitory medium that may be used to store information including images, training data, ML technique parameters, device adaptation functions, data, or transitory or non-transitory computer-executable instructions (e.g., stored in any format) capable of being accessed by the processing circuitry 512, or any other type of computer device. For instance, the computer program instructions can be accessed by the processing circuitry 512, read from the ROM, or any other suitable memory location, and loaded into the RAM for execution by the processing circuitry 512.

The storage device 516 may constitute a drive unit that includes a transitory or non-transitory machine-readable medium on which is stored one or more sets of transitory or non-transitory instructions and data structures (e.g., software) embodying or utilized by any one or more of the methodologies or functions described herein (including, in various examples, the treatment processing logic 520 and the user interface 542). The instructions may also reside, completely or at least partially, within the memory 514 and/or within the processing circuitry 512 during execution thereof by the radiotherapy processing computing system 510, with the memory 514 and the processing circuitry 512 also constituting transitory or non-transitory machine-readable media.

The memory 514 and the storage device 516 may constitute a non-transitory computer-readable medium. For example, the memory 514 and the storage device 516 may store or load transitory or non-transitory instructions for one or more software applications on the computer-readable medium. Software applications stored or loaded with the memory 514 and the storage device 516 may include, for example, an operating system for common computer systems as well as for software-controlled devices. The radiotherapy processing computing system 510 may also operate a variety of software programs comprising software code for implementing the treatment processing logic 520 and the user interface 542. Further, the memory 514 and the storage device 516 may store or load an entire software application, part of a software application, or code or data that is associated with a software application, which is executable by the processing circuitry 512. In a further example, the memory 514 and the storage device 516 may store, load, and manipulate one or more radiation therapy treatment plans, imaging data, segmentation data, treatment visualizations, histograms or measurements, and the like. It is contemplated that software programs may be stored not only on the storage device 516 and the memory 514 but also on a removable computer medium, such as a hard drive, a computer disk, a CD-ROM, a DVD, a Blu-Ray DVD, USB flash drive, a SD card, a memory stick, or any other suitable medium; such software programs may also be communicated or received over a network.

Although not depicted, the radiotherapy processing computing system 510 may include a communication interface, network interface card, and communications circuitry. An example communication interface may include, for example, a network adaptor, a cable connector, a serial connector, a USB connector, a parallel connector, a high-speed data transmission adaptor (e.g., such as fiber, USB 5.0, thunderbolt, and the like), a wireless network adaptor (e.g., such as a IEEE 802.11/Wi-Fi adapter), a telecommunication adapter (e.g., to communicate with 5G, 4G/LTE, and 5G, networks and the like), and the like. Such a communication interface may include one or more digital and/or analog communication devices that permit a machine to communicate with other machines and devices, such as remotely located components, via a network. The network may provide the functionality of a local area network (LAN), a wireless network, a cloud computing environment (e.g., software as a service, platform as a service, infrastructure as a service, etc.), a client-server, a wide area network (WAN), and the like. For example, the network may be a LAN or a WAN that may include other systems (including additional image processing computing systems or image-based components associated with medical imaging or radiotherapy operations).

In an example, the radiotherapy processing computing system 510 may obtain image data 552 from the image data source 550 (e.g., CT, PET, and/or MR images), for hosting on the storage device 516 and the memory 514. In yet another example, the software programs may substitute functions of the patient images such as signed distance functions or processed versions of the images that emphasize some aspect of the image information.

In an example, the radiotherapy processing computing system 510 may obtain or communicate image data 552 from or to image data source 550. In further examples, the treatment data source 560 receives or updates the planning data 562 as a result of radiotherapy device parameter adjustments or segment adaptation or detecting movement of an object (e.g., a target locus).

The processing circuitry 512 may be communicatively coupled to the memory 514 and the storage device 516, and the processing circuitry 512 may be configured to execute computer-executable instructions stored thereon from either the memory 514 or the storage device 516. The processing circuitry 512 may execute instructions to cause medical images from the image data 552 to be received or obtained in memory 514 and processed using the treatment processing logic 520.

In addition, the processing circuitry 512 may utilize software programs to generate intermediate data such as updated parameters to be used, for example, by a neural network model, a deep learning neural network model, a regression technique comprising a support vector machine or random forest, machine learning model, or other aspects involved with generation of device parameter adjustments or segment adaptation, as discussed herein. Further, such software programs may utilize the treatment processing logic 520 to produce updated radiotherapy parameters to provide to the treatment data source 560 to modify a dose delivered to a target within a given fraction and/or for presentation on output device 546, using the techniques further discussed herein. The processing circuitry 512 may subsequently then transmit the updated radiotherapy parameters via a communication interface and the network to the treatment device 580, where the updated parameters will be used to treat a patient with radiation via the treatment device 580. Radiotherapy parameters (also referred to as control points) may include, for each segment or portion of a given treatment fraction, MLC positions and settings, gantry angle, radiation dose amount (e.g., amount of monitor units (MU)), radiotherapy beam direction, radiation beam size, arc placement, beam on and off time duration, machine parameters, gantry speed, MRI pulse sequence, any combination thereof, and so forth.

In an example, the image data 552 may include one or more MR images (e.g., 2D MM, 5D MRI, 2D streaming MRI, 4D MRI, 4D volumetric MRI, 4D cine MRI, etc.), functional MRI images (e.g., fMRI, DCE-MRI, diffusion MRI), Computed Tomography (CT) images (e.g., 2D CT, 2D Cone beam CT, 5D CT, 5D CBCT, 4D CT, 4DCBCT), ultrasound images (e.g., 2D ultrasound, 5D ultrasound, 4D ultrasound), Positron Emission Tomography (PET) images, X-ray images, fluoroscopic images, radiotherapy portal images, Single-Photo Emission Computed Tomography (SPECT) images, computer-generated synthetic images (e.g., pseudo-CT images), radio-beacons, laser scanning of the patient surface, and the like. Further, the image data 552 may also include or be associated with medical image processing data, for instance, training images, ground truth images, contoured images, and dose images. In other examples, an equivalent representation of an anatomical area may be represented in non-image formats (e.g., coordinates, mappings, etc.).

In an example, the image data 552 may be received from the image acquisition device 570 and stored in one or more of the image data sources 550 (e.g., a Picture Archiving and Communication System (PACS), a Vendor Neutral Archive (VNA), a medical record or information system, a data warehouse, etc.). Accordingly, the image acquisition device 570 may comprise an MRI imaging device, a CT imaging device, a PET imaging device, an ultrasound imaging device, a fluoroscopic device, a SPECT imaging device, an integrated Linear Accelerator and MRI imaging device, CBCT imaging device, or other medical imaging devices for obtaining the medical images of the patient. The image data 552 may be received and stored in any type of data or any type of format (e.g., in a Digital Imaging and Communications in Medicine (DICOM) format) that the image acquisition device 570 and the radiotherapy processing computing system 510 may use to perform operations consistent with the disclosed embodiments. Further, in some examples, the models discussed herein may be trained to process the original image data format or a derivation thereof.

In an example, the image acquisition device 570 may be integrated with the treatment device 580 as a single apparatus (e.g., an MRI device combined with a linear accelerator, also referred to as an "MRI-Linac"). Such an MRI-Linac can be used, for example, to determine a location of a target in the patient, so as to direct the radiation beam accurately according to the radiation therapy treatment plan to a predetermined target. For instance, a radiation therapy treatment plan may provide information about a particular radiation dose to be applied to each patient. The radiation therapy treatment plan may also include other radiotherapy information and radiotherapy device parameters, such as beam angles, dose-volume-histogram information, the number of radiation beams to be used during therapy, the dose per beam, and the like. The MM-Linac can be used to compute, generate, and/or update a patient deformation model to deform image portions of a 5D or 2D image of a patient corresponding to a given beam delivery segment. The MRI-Linac can be used to provide real-time patient images (or subsets of patient images) and machine settings or parameters at various increments/intervals of a treatment fraction to continuously or periodically compute dose for the increments/intervals and determine a real-time dose accumulation based on such computed doses.

The radiotherapy processing computing system 510 may communicate with an external database through a network to send/receive a plurality of various types of data related to image processing and radiotherapy operations. For example, an external database may include machine data (including device constraints) that provides information associated with the treatment device 580, the image acquisition device 570, or other machines relevant to radiotherapy or medical procedures. Machine data information may include radiation beam size, arc placement, beam on and off time duration, machine parameters, segments, MLC configuration, gantry speed, MRI pulse sequence, and the like. The external database may be a storage device and may be equipped with appropriate database administration software programs. Further, such databases or data sources may include a plurality of devices or systems located either in a central or a distributed manner.

The radiotherapy processing computing system 510 can collect and obtain data, and communicate with other systems, via a network using one or more communication interfaces, which are communicatively coupled to the processing circuitry 512 and the memory 514. For instance, a communication interface may provide communication connections between the radiotherapy processing computing system 510 and radiotherapy system components (e.g., permitting the exchange of data with external devices). For instance, the communication interface may, in some examples, have appropriate interfacing circuitry from an output device 546 or an input device 548 to connect to the user interface 542, which may be a hardware keyboard, a keypad, or a touch screen through which a user may input information into the radiotherapy system.

As an example, the output device 546 may include a display device that outputs a representation of the user interface 542 and one or more aspects, visualizations, or representations of the medical images, the treatment plans, and statuses of training, generation, verification, or implementation of such plans. The output device 546 may include one or more display screens that display medical images, interface information, treatment planning parameters (e.g., contours, dosages, beam angles, labels, maps, etc.), treatment plans, image portions that are identified and deformed for a given treatment segment, a target, localizing a target and/or tracking a target, or any related information to the user. The output device 546 may provide to a user visualization of movement of the target object or therapy locus during delivery of the radiotherapy treatment fraction.

The input device 548 connected to the user interface 542 may be a keyboard, a keypad, a touch screen or any type of device using which a user may input information to the radiotherapy system 500. Alternatively, the output device 546, the input device 548, and features of the user interface 542 may be integrated into a single device such as a smartphone or tablet computer (e.g., Apple iPad®, Lenovo Thinkpad®, Samsung Galaxy®, etc.).

Furthermore, any and all components of the radiotherapy system 500 may be implemented as a virtual machine (e.g., via VMWare, Hyper-V, and the like virtualization platforms) or independent devices. For instance, a virtual machine can be software that functions as hardware. Therefore, a virtual machine can include at least one or more virtual processors, one or more virtual memories, and one or more virtual communication interfaces that together function as hardware. For example, the radiotherapy processing computing system 510, the image data sources 550, or like components, may be implemented as a virtual machine or within a cloud-based virtualization environment.

The image acquisition device 570 can be configured to acquire one or more images of the patient's anatomy for a region of interest (e.g., a target organ, a target tumour or both). Each image, typically a 2D image or slice, can include one or more parameters (e.g., a 2D slice thickness, an orientation, and a location, etc.). In an example, the image acquisition device 570 can acquire a 2D slice in any orientation. For example, an orientation of the 2D slice can include a sagittal orientation, a coronal orientation, or an axial orientation. The processing circuitry 512 can adjust one or more parameters, such as the thickness and/or orientation of the 2D slice, to include the target organ and/or target tumour. In an example, 2D slices can be determined from information such as a 5D CBCT or CT, or MRI volume. Such 2D slices can be acquired by the image acquisition device 570 in "near real-time" while a patient is undergoing radiation therapy treatment, for example, when using the treatment device 580 (with "near real-time" meaning acquiring the data without (or with minimal) lag between image acquisition and treatment, as known in the art). In an example, 5D volumetric representation of a region of interest can be generated using a stack of one or more 2D slices.

Figure 6:
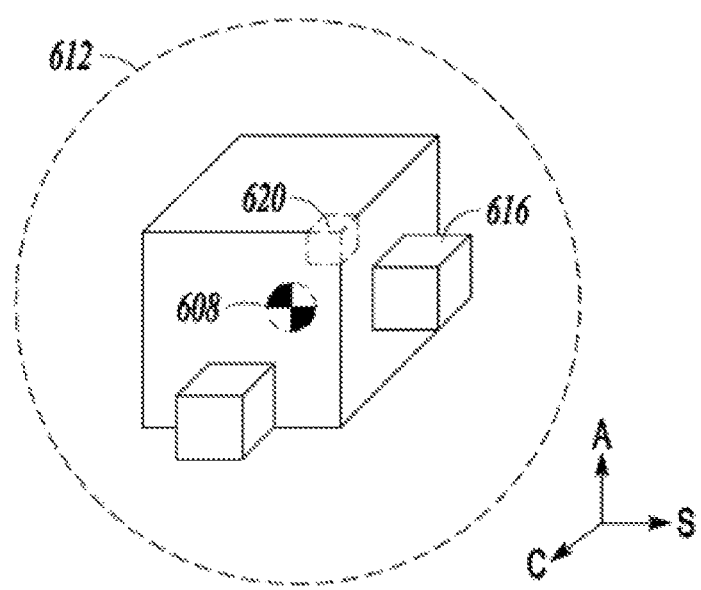
FIG. 6 illustrates generally a view of a target locus, such as a tumor region, such as can be obtained using a volumetric imaging technique, according to some embodiments.

FIG. 6 illustrates generally a view of an object or target locus 616, such as a tumor region to be treated using radiation therapy. Information indicative of the target locus 616 can be obtained using a volumetric imaging technique. The representation in FIG. 6 is shown has having rectangular facets merely for purposes of illustration, and an actual target locus 616 may include curved or irregular surfaces. A region of interest 612 can be imaged, such as using one or more of MR imaging, CT imaging, pseudo-CT image visualization, portal imaging, ultrasound imaging, or other techniques. The target locus 616 can be identified such as using automated, manual, or semi-automated image segmentation techniques. For example, a specified label can be assigned to voxels (e.g., a voxel 620) to identify a locus or group of voxels comprising a radiation therapy target. As an illustrative example, a contrast value for a voxel 620 can be compared to adjacent voxels, and an edge of a tumor or other region can be identified such as using contrast information. Other regions can also be identified such as nearby organs or locations of other features.

Various features of a target locus can be determined such as one or more edge locations (e.g., using an edge detection or edge identification technique). For example, a position of the target locus 616 can be identified by determining a spatial centroid 608 of the target locus 616. The use of a centroid 608 as an extracted feature is illustrative and other features can be used for tracking target locus 616 motion, such as a manually-identified or automatically-determined location of a point, surface, or edge of the target locus 616. In yet another example, an implantable or external seed fiducial can be used, such as providing an indicium in obtained imaging information.

The target locus 616 and one or more corresponding features such as the centroid 608 can be identified during treatment planning imaging, such as inter-fractionally (e.g., between radiation therapy delivery sessions) or just prior to beginning a radiation therapy delivery session. Volumetric imaging information comprising the target locus 616 can be referred to as a "reference image." As mentioned above, a challenge can exist because image acquisition and processing latency may preclude "real time" acquisition of volumetric imaging information during radiation treatment. Accordingly, intra-fractional image acquisition (such as during or between radiation therapy deliveries in a radiation therapy session) can include more rapid acquisition of imaging slices (including one or more of one-dimensional profiles, two-dimensional slices, cine images, or three-dimensional volumes comprising a sub-volume or sub-region of an earlier-imaged volumetric region). Information indicative of a portion of the target locus obtained rapidly from one or more imaging slices can be compared to information obtained from an earlier-acquired volumetric reference image to update a therapy protocol, such as to adjust therapy due to movement of the target locus. The imaging modality used for obtaining or generating the volumetric reference image need not be the same as is used for intra-fractional imaging.

In another example, the target locus 616 need not be segmented or otherwise identified in the volumetric reference image. Use of the phrase "target locus" is merely illustrative of a target within the region of interest such as a portion or an entirety of a tumor to be treated or other anatomical structures such as organs near the tumor. In addition to, or instead of segmentation of the target locus 616, various techniques as described herein can be performed such as including spatially registering a portion of the volumetric reference image (e.g., a specified region of interest) or an entirety of the volumetric reference image with other imaging information such as using voxel values including contrast or grayscale values. For example, such spatial registration can include three-dimensional (e.g., volumetric) registration with one or more two-dimensional imaging slices (e.g., 3D-to-2D registration), or other techniques.

FIG. 7A and FIG. 7B illustrate views of an imaging acquisition plane 712A (in FIG. 7A) of a target locus 716 and a corresponding acquired imaging slice 714A (in FIG. 7B) corresponding to a first imaging plane orientation intersecting the target locus 716 along a line 706A. As an illustrative example, FIG. 7A can represent a sagittal orientation of the image acquisition plane 712A and corresponding slice 714A. An imaging "slice" can include two-dimensional pixel imaging information or three-dimensional imaging information, such as having a small finite thickness as shown illustratively in FIG. 7B. A portion 718A of the target locus in the imaging slice 714A can be identified, such as again using a segmentation technique, for example using a discrete dynamic contour, snake, or level set, or a registration-based technique.

Figure 7E:
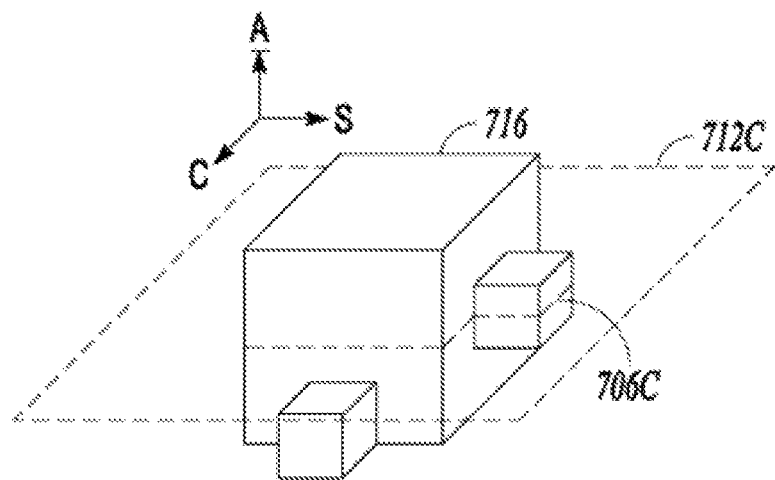
FIG. 7E and FIG. 7F illustrate views of an imaging acquisition plane (in FIG. 7E) and a corresponding acquired imaging slice (in FIG. 7F) corresponding to a third imaging plane orientation, such as can be orthogonal to one or more of the first and second imaging plane orientations mentioned above in relation to FIG. 7A, FIG. 7B, FIG. 7C, and FIG. 7D, according to some embodiments.
Figure 7F:
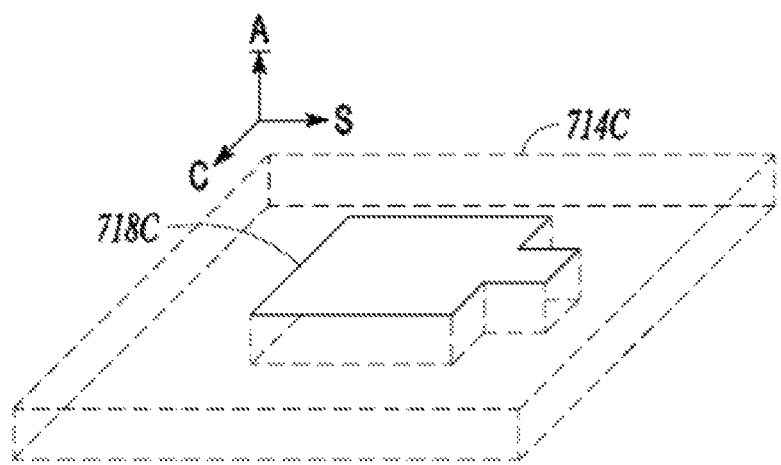

A series of imaging slices can be obtained, such as including different imaging acquisition plane orientations as shown in FIG. 7C, FIG. 7D, FIG. 7E, and FIG. 7F. For example, FIG. 7C and FIG. 7D illustrate views of an imaging acquisition plane 712B (in FIG. 7C) intersecting the target locus 716 along a line 706B and a corresponding acquired imaging slice 714B (in FIG. 7D) including a different portion 718B of the target locus 716, corresponding to a second imaging plane orientation, such as can be orthogonal to the first imaging plane orientation mentioned above in relation to FIG. 7A and FIG. 7B. As an illustration, FIG. 7C and FIG. 7D can correspond to a coronal plane. FIG. 7E and FIG. 7F illustrate views of an imaging acquisition plane 712C (in FIG. 7E) intersecting the target locus 716 along a line 706C and a corresponding acquired imaging slice 714C (in FIG. 7F) including yet another different portion 718C of the target locus 716, corresponding to a third imaging plane orientation, such as can be orthogonal to one or more of the first and second imaging plane orientations mentioned above in relation to FIG. 7A, FIG. 7B, FIG. 7C, and FIG. 7D. As an illustration, FIG. 7E and FIG. 7F can correspond to an axial imaging plane. The imaging slices of FIG. 7A, FIG. 7B, FIG. 7C, FIG. 7D, FIG. 7E, and FIG. 7F are shown as two-dimensional planes that are orthogonal to each other. However, as mentioned in relation to other examples herein, the slices need not be planar nor orthogonal. Each acquired imaging slice can be processed, including processing of one or more slices in parallel with an acquisition of an imaging slice. For example, such processing can include sampled information from a volumetric reference image, such as corresponding to a plane or region of the acquired imaging slice.

In one approach, a feature extracted from one or more of the imaging slices 714A, 714B, or 714C can be compared with imaging information extracted from a volumetric reference image. For example, a segmented portion of the target locus 616 from the volumetric reference image, or a region encapsulating the target locus and surrounding tissues, can be spatially registered with a corresponding imaging slice 714A, 714B, or 714C to determine if the target locus has shifted. However, comparing a feature extracted from a single two-dimensional imaging slice with a corresponding feature from the volumetric reference image can present challenges. For example, FIG. 8A illustrates generally a series of imaging acquisition planes 812A, 812B, and 812C, such as can be obtained as a target locus 816 moves from one imaging acquisition instance to another. At time $t_{i-2}$, a line 806A where the imaging acquisition plane intersects the target locus 816 is roughly centered, and at time $t_{i-1}$, the line 806B is shifted, and at time the line 806C is shifted further. Imaging slices obtained at times $t_i$, $t_{i-1}$, $t_{i-2}$, . . . can be labeled as $S_i$, $S_{i-1}$, $S_{i-2}$, . . . generally.

If the motion of the target locus is out-of-plane, the centroid or other feature location may not appear to shift significantly from image-to-image, even though the target locus has moved significantly, or the target locus may appear to deform, making interpretation of motion difficult. However, such out-of-plane motion can be properly tracked such as by one or more of varying an orientation of successively-acquired imaging slices (e.g., as shown in FIG. 8C and elsewhere), or varying or compensating for a non-planar shape of the imaging acquisition region so that the imaging slices are not represented as perfectly planar in a three-dimensional sense (e.g., as shown in FIG. 8B). For example, FIG. 8B illustrates generally a series of imaging slices 813A, 813B, and 813C, such as can include a curved shape. Generally, even when referring to image acquisition "planes," the techniques described herein can be used with other slice geometries such as the curved slices of FIG. 8B. As an illustrative example, MR imaging information may be available as planar slices, and a transformation can be applied to the planar slices to obtain surfaces that curve in a three-dimensional sense, such as to help capture or correct for distortion across the imaging field such as to compensate for inhomogeneity in an established magnetic field. As another illustrative example, FIG. 8C illustrates generally a series of imaging acquisition planes 815A, 815B, and 815C such as can include different orientations that need not each be orthogonal.

As mentioned above, if imaging slices are acquired sequentially in time, the target locus is likely to shift between successive image acquisitions. FIG. 9A illustrates generally a series of two imaging slices, such as including a target locus that is displaced between first and second imaging slices. The example of two sequentially-acquired imaging slices is illustrative. The techniques described herein are also generally applicable to sequences of more than two imaging slices (or even a single imaging slice analyzed with respect to a portion or an entirety of the reference volumetric imaging information).

An imaging slice 914A (e.g., Si) can include a portion 918A of the target locus, and a second imaging slice 914B ($S_{i-1}$, such as acquired earlier in time) can include a second portion 918B. The second portion 918B appears displaced with respect to the first portion 918A by a displacement 920. Because the displacement 920 is generally an unknown value or vector, various techniques can be used such as to spatially register the first and second portions 918A and 918B. As shown in FIG. 9B, a spatially-registered slice 914C can include an adjusted location of a portion 918C of the target locus. Notationally, a set or series of acquired imaging slices can be labeled $S_i, S_{i-1}, S_{i-2}, \ldots, S_{i-n}$ with $S_i$ corresponding to the most recently-acquired slice for processing and corresponding to the earliest-acquired slice for processing. A series of spatially-registered imaging slices can be labeled $S_i, S'_{i-1}, S'_{i-2}, \ldots S'_{i-n}$.

Figure 10:
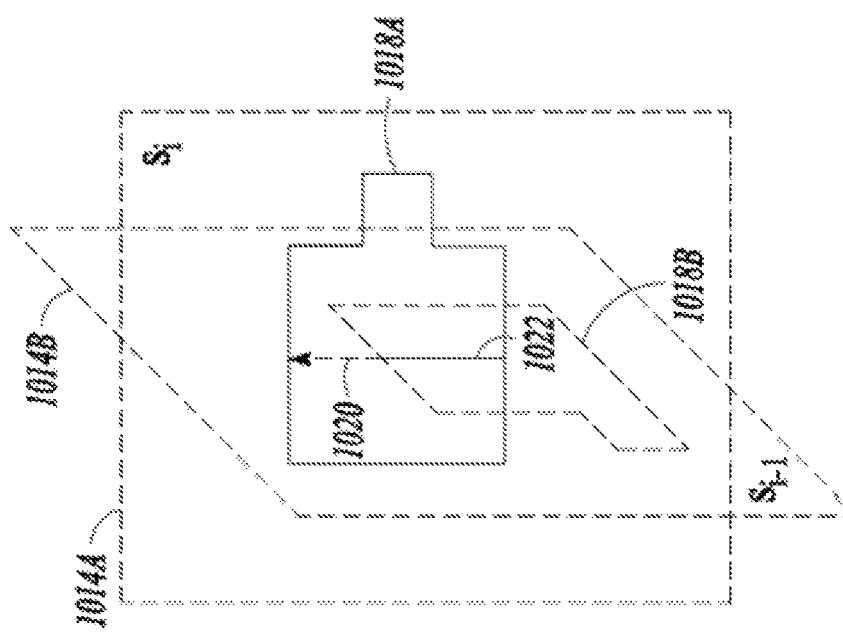
FIG. 10 illustrates generally a technique that can include spatially registering segmented portions of a target locus, according to some embodiments.

FIG. 10 illustrates generally a technique that can include spatially registering segmented portions of a target locus from two (or more) imaging slices $S_i, S_{i-1}, S_{i-2}, \ldots, S_{i-n}$. In one approach, a metric can be defined that quantifies how well the two portions 1018A and 1018B of a target locus are aligned (or more generally, how well two imaging slices or imaging volumes are aligned), such as the similarity between the pixels along the intersection line 1022 joining the first portion 1018A and the shifted second portion 1018B. Examples of such metrics include one-dimensional normalized cross-correlation or mutual information. An automated optimization technique can be executed to find translations of the second portion 1018B that provide the optimal value of the metric. Masks can be used to limit the calculation to the most relevant pixels only, such as pixels close to the target of interest. This first approach generally relies on the planes having a common intersection line.

Another approach can include creating three-dimensional (3D) voxel images, such as having a first image corresponding to a first slice orientation including populated voxels corresponding to a portion of the target locus within the slice and zero-valued voxels outside the slice, and a second image of a second slice orientation including its own populated voxels corresponding to the portion of the target locus in the second image. As an illustrative example, MR imaging slices generally have a finite thickness, such as corresponding to about 5 millimeters. A finite slice thickness can be taken into account by assigning voxels with slice information within the actual slice thickness using two-dimensional (2D) pixel information extracted from an MR imaging slice. A 3D registration technique can be used find the optimal translation between the two 3D images, and masks can be used to exclude voxels that do not contain slice information. The 3D registration approach also generally relies on having a common intersection line. An illustrative example of three-dimensionally-registered imaging slices is shown illustratively in FIG. 11A.

In yet another approach, a prediction technique can be applied to a prior imaging slice to find the most likely position of a portion of the target locus for the prior imaging slice orientation but having the same time stamp as the current or a more-recently-acquired imaging slice. Various techniques can be used for such prediction, such as Kernel Density Estimation, a neural network, a deep learning neural network model, regression technique comprising a support vector machine or random forest, or a template matching technique. Prediction can be particularly effective if a motion of the target locus is highly periodic in nature, such as associated with respiratory motion. Although using a prediction is an approximation only, it can also be used in combination with the image-based methods described above and elsewhere herein. A prediction-based approach does not rely on image acquisition planes having a common intersection line, and so prediction techniques can be used when parallel slices are acquired.

In yet another approach, when fast perpendicular MR-imaging slices are acquired, dark lines can appear in the current image in the location where the previous image was excited and not yet fully relaxed to equilibrium. Because the excited magnetic dipoles from the previous slice follow the moving anatomy, a visible previously-excited region (e.g., an excitation line) can be used as an anchor to align previous slices with later-acquired imaging information. This can be taken into account implicitly with the other techniques mentioned above, because such darkened regions as pixel or voxel features can affect registration, or explicitly, such as by identifying or explicitly determining the location of such darkened regions in acquired imaging slices. For example, a peak-detection technique can be used to find points along the center of the darkened regions, and a line (straight or curved) can be found that provides a best fit to these points. Various examples described in this document refer to registration between images, such as including registration of a segmented portion of a first image with a segmented portion or other identified features of a second image (or a series of images). Generally, a registration between two images can include a moving and a fixed image. The goal can be to determine a position or transformation of the moving image such that it best fits the fixed image. "Move" can mean, for example, to shift the moving image spatially in one or more dimensions (translations only), shift and rotate the moving image, or even deform the moving image. The degrees of freedom available to move the moving image can be referred to as "optimization parameters," which, as an illustrative example, can include two degrees of freedom in the case of shift only with two 2D images, or 6 degrees of freedom for shifts plus rotations for 3D images. Even though we may be generally referring to 3D image registration, "optimization parameters" can still be generally referred to as "shift values" without loss of generality.

For a given set of optimization parameters, a metric can define a "goodness" of a determined overlap between the moving and fixed images. Various examples can include determining a normalized cross-correlation or mutual information (such as using voxel or pixel values as input values), and such techniques can provide an indication of an optimal value of the metric when the images match perfectly. The nature of the underlying imaging technique can be helpful in establishing which metric to use. For example, a mutual information technique can be used for images obtained using different modalities such as positron emission tomography (PET) and CT imaging.

An optimization technique can be used to find the shift values that optimize the metric between the moving and fixed images, such as to identify shift values that give the best match between the two images. Different optimizers that can be used can include gradient descent, simulating annealing, trust-region gradient descent, or one or more other techniques. In some cases, there may be deformations between the images, but it is not always necessary to optimize deformation vector fields and take these into account, because optimization of deformation information can result in one or more of undesired latency or can erode stability of the optimization technique. Calculation of the metric can be limited to a specified region of interest, such as referred to as a "mask." For example, assuming there is negligible deformation in the region of interest, one or more of translations or rotations, without deformation, can be used to determine shift values that are locally optimal in the specified region of interest.

Generally, if one or more 2D imaging slices are available, a motion of a radiation therapy target can be determined between a current 2D slice (such as an MR imaging slice) and an initial 3D volume (e.g., a reference volumetric image). As an illustrative example, the 3D volume can also correspond to a particular phase of respiration to reduce respiration blurring, which can be accomplished either with gated or triggered imaging (e.g., triggered imaging), or by extracting the 3D volumetric image from four-dimensional imaging information at a particular phase (e.g., extracting a 3D volumetric snapshot from a 4D imaging series, such as 4D imaging information obtained using MR imaging).

In one approach, the target itself can be identified in an imaging slice. However, while segmentation is mentioned elsewhere herein, the techniques described herein are also applicable if segmentation or other feature extraction is not performed. As an illustrative example, a best fit of grayscale values can be determined between one or more later-acquired imaging slices and an earlier-acquired reference 3D image. A target does not need to actually be in the image, but a region of interest can be specified, such as can include a portion of the target, or the target plus a margin, or just an arbitrary region of interest without the target.

In one approach, a 2D/3D registration can be performed to find a relative shift between a current imaging slice and the reference volume. The 3D image can represent the 'moving image' and a 2D slice can represent the 'fixed image' in relation to the registration technique. Generally, the location of the target can be identified in the 3D image, and applying the relative shift to the earlier target location can provide an estimate of an updated location of the target, such as within a three-dimensional coordinate frame. Such an estimate can be performed without requiring determination of deformation, and may even be performed without use of rotational parameters, such as to increase execution efficiency of the optimization technique. Such simplifying assumptions can be applied such as when registering a 3D reference image to one or more 2D imaging slices.

A specified region of interest can be used to define a mask around the target plus a margin, for example (though the region of interest need not include the target or an entirety of the target). Deformation may be present, but as an illustrative example, if the margin is small, deformation will also be small (e.g., negligible) and a shift of the target itself can be determined using a registration technique ignoring deformation. In this manner, a single plane technique (e.g., a technique where the imaging slice is the fixed image) can still provide information indicative of a shift in three dimensions. Such a technique is robust when there are enough features in the images to "lock in" the registration in three dimensions—the registration converges to a well-defined optimum—though the features need not be extracted or segmented.

In one approach, a normalized cross-correlation of the gradient of the images can be used as a registration metric, since such a technique tends to match image edges and is less sensitive to absolute grayscale values that can differ from image to image. A single imaging slice or plane may, in some cases, not be sufficiently robust to establish a shift with a clear optimal value (colloquially, 'lock in'). Accordingly, additional slices can be useful to help lock in all directions, for example using a current sagittal and a previously-acquired coronal slice, or vice-versa, as illustrative examples. As a count of slices used for registration increases, whether parallel, orthogonal, or in non-parallel and non-orthogonal planes, more information is available to perform a registration between the reference volumetric image and the later-acquired imaging slices, which improves the robustness of the resulting shift parameter determination.

Figure 12:
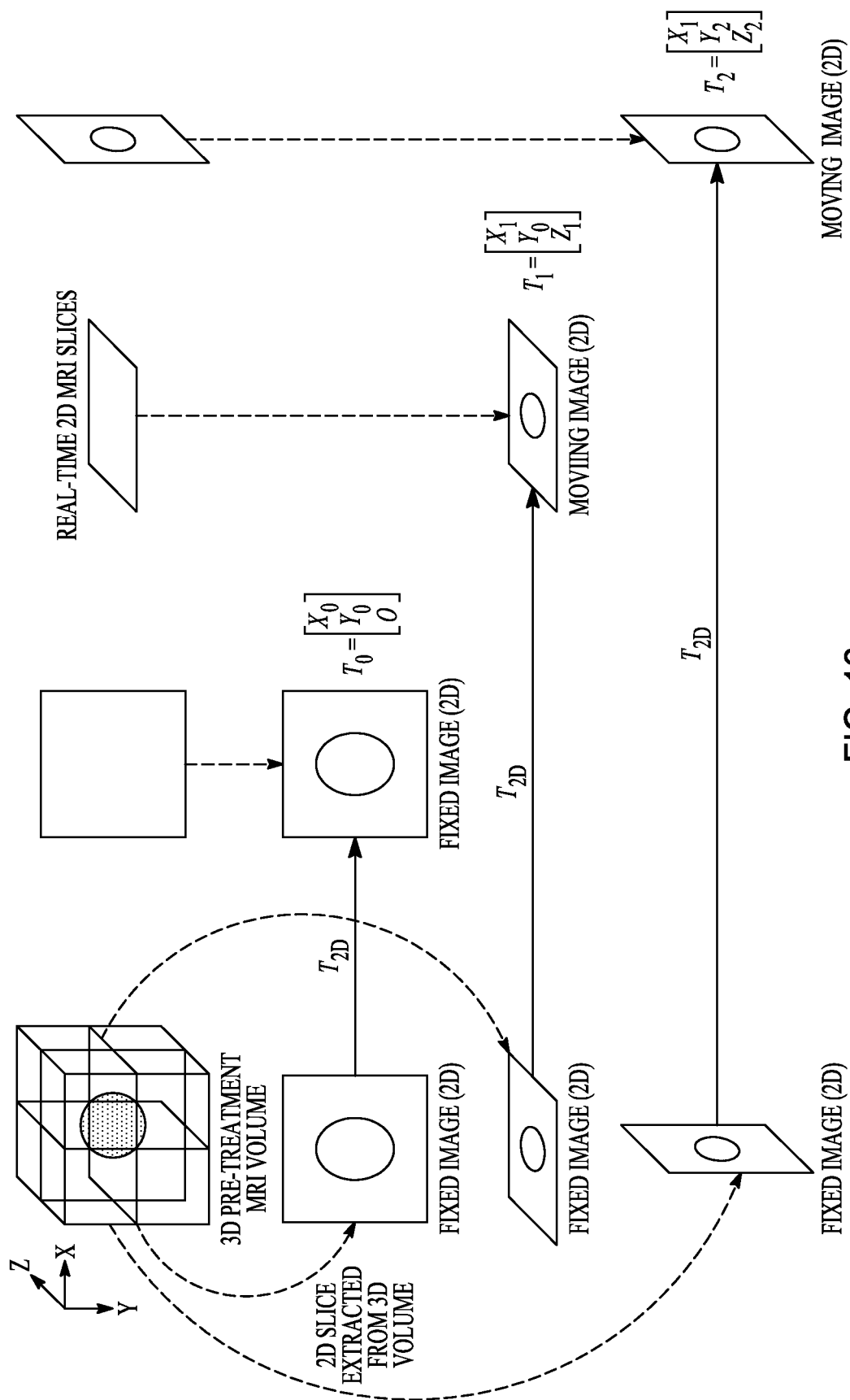
FIG. 12 illustrates a second technique for determining movement of an object, according to some embodiments.

FIG. 12 illustrates a second technique for determining movement of an object, according to some embodiments. Specifically, as shown in FIG. 12, a first slice (e.g., a 2D cine image) in which an object is depicted and which is defined along a first plane (e.g., the sagittal plane) can be captured in real-time at a first time point during a radiotherapy treatment session. The first slice is registered with a portion of the volumetric image depicting the object to determine movement of the object along first and second directions. For example, the corresponding plane (e.g., the sagittal plane) can be extracted from the pre-treatment 3D image and registered with the captured first slice to determine movement of the object along first and second directions. As an example, the first and second directions can include the superior/inferior direction and along the anterior/posterior direction. The left/right movement of the object (e.g., movement along the third direction) may be missing from registration of the first slice with the volumetric portion. In this case, movement of the object along the missing third direction (e.g., the left/right direction) can be obtained based on a second slice (e.g., a 2D cine image) in which the object was depicted from a previous time point during the radiotherapy treatment session. The second slice may be defined along the coronal plane and, when registered against a corresponding plane in the volumetric image, provides movement along the left/right directions. In this way, movement of the object at the current time point in the radiotherapy treatment session, along the first, second, and third directions, can be determined using a slice defined along a first plane corresponding to the current time point and using a previously captured slice defined along a second plane.

In some cases, the volumetric image is defined as the moving image for registration purposes and the 2D images captured during the radiotherapy treatment session are defined as the fixed images. At a later or sequentially next time point in the radiotherapy treatment session, a third slice (e.g., a 2D cine image) in which the object is depicted and which is defined along the second plane is captured. The third slice is registered with a portion of the volumetric image depicting the object to determine movement of the object along first and third directions. For example, the corresponding plane (e.g., the coronal plane) can be extracted from the pre-treatment 3D image and registered with the captured third slice to determine movement of the object along first and third directions. As an example, the first and third directions can include the superior/inferior direction and along the left/right direction, respectively. The anterior/posterior movement of the object (e.g., movement along the second direction) may be missing from registration of the third slice with the volumetric portion. In this case, movement of the object along the missing second direction (e.g., the anterior/posterior direction) can be obtained based on a fourth slice (e.g., a 2D cine image) in which the object was depicted from a previous time point during the radiotherapy treatment session. The fourth slice may be defined along the sagittal plane and, when registered against a corresponding plane in the volumetric image, provides movement along the anterior/posterior directions. In this way, movement of the object at the current time point in the radiotherapy treatment session, along the first, second, and third directions, can be determined using a slice defined along a first plane corresponding to the current time point and using a previously captured slice defined along a second plane.

Figure 13:
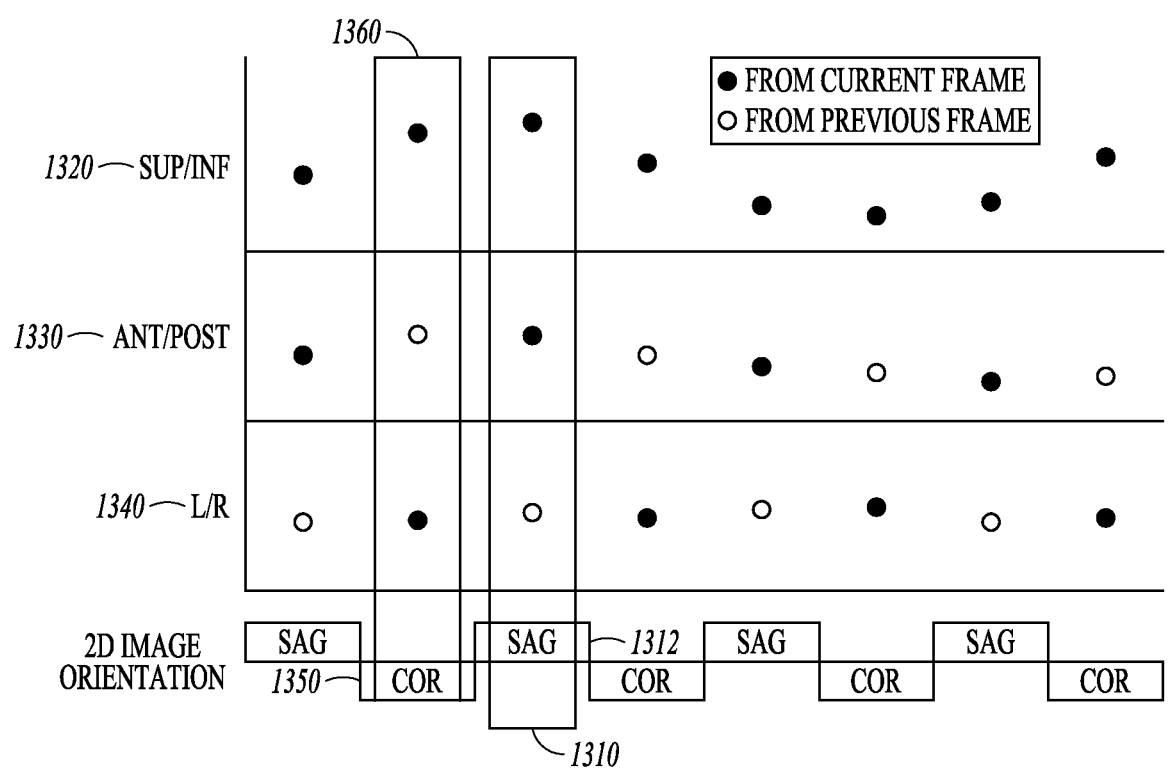
FIG. 13 illustrates a timing diagram for determining movement of the object according to the second technique, according to some embodiments.

FIG. 13 illustrates a timing diagram for determining movement of the object according to the second technique, according to some embodiments. As shown in FIG. 13, during a first time point 1310 in a radiotherapy treatment session, a sagittal image 1312 (e.g., a 2D cine image along the sagittal plane) is captured. This sagittal image 1312 is registered with a pre-treatment 3D volumetric image. As a result of this registration, movement of the object depicted in the sagittal image 1312 captured during the first time point can be determined along the first direction 1320 and the second direction 1330 (e.g., along the superior/inferior directions and along the anterior/posterior directions). Movement along the left/right direction 1340 is missing. To recover the missing movement information, a coronal image 1350 (e.g., a 2D cine image along the coronal plane) is retrieved that was captured during one or more prior time points 1360 in the same radiotherapy treatment session. The previously captured coronal image 1350 is registered against the same 3D volumetric image to provide the movement along the left/right direction 1340 (e.g., the left/right movement). In this way, movement of the object along three directions can be determined using a currently captured image defined along a first plane and a previously captured image defined along a second plane.

Figure 14:
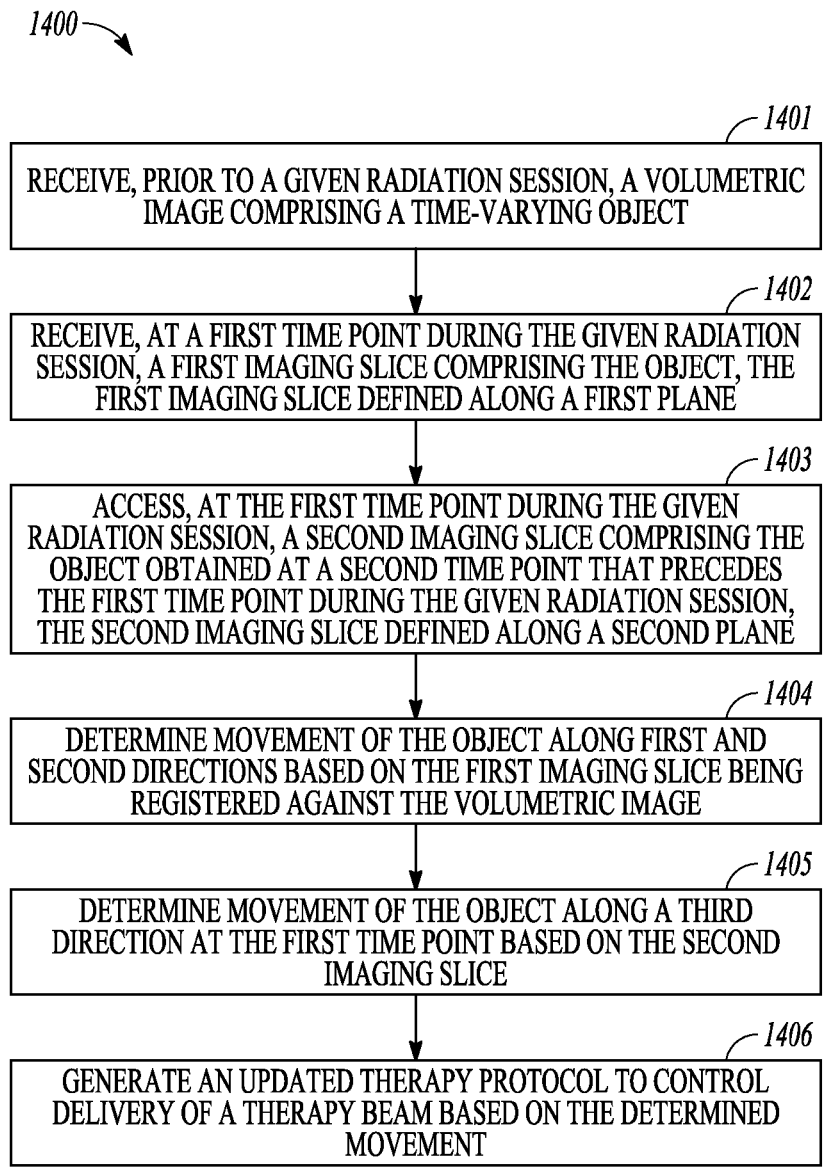
FIG. 14 is a flow diagram for determining movement of the object according to the second technique, according to some embodiments.

FIG. 14 is a flow diagram 1400 for determining movement of the object according to the second technique, according to some embodiments. The operations discussed in FIG. 14 can be performed in sequence, in parallel, skipped, or out of order. The operations discussed in FIG. 14 can be performed by computing system 510 (FIG. 5).

At operation 1401, the computing system 510 receives, prior to a given radiation session, a volumetric image comprising a time-varying object.

At operation 1402, the computing system 510 receives, at a first time point during the given radiation session, a first imaging slice comprising the object. The first imaging slice is defined along a first plane.

At operation 1403, the computing system 510 accesses, at the first time point during the given radiation session, a second imaging slice comprising the object, the second imaging slice having been obtained at a second time point that precedes the first time point during the given radiation session and being defined along a second plane.

At operation 1404, the computing system 510 determines movement of the object along first and second directions based on the first imaging slice being registered against the volumetric image.

At operation 1405, the computing system 510 determines movement of the object along a third direction at the first time point based on the second imaging slice.

At operation 1406, the computing system 510 generates an updated therapy protocol to control delivery of a therapy beam based on the determined movement.

The registration can include sweeping a 3D volume across one or more imaging slices, or the slices can be inserted into a 3D volume as mentioned elsewhere herein, in which case a 3D-to-3D registration technique can be used (such as suppressing or ignoring registration of unfilled voxels). A multiple-slice technique works well such as if the slices are acquired in rapid succession, for example, less than about 50 ms between instants corresponding to acquired slices. If a longer duration occurs between imaging slice acquisitions, then the older slices may become 'stale.' However, such slices can still be temporally re-aligned such as using either a) a prediction technique, such as where the target motion is periodic in nature; b) aligning the excitation lines provided by the imaging modality (e.g., excitation lines visible from MR imaging acquisition), for example by fitting a line through such excitation lines as mentioned elsewhere herein; or c) by spatially-registering the stale imaging slice so that it fits with the current slice using a metric that is calculated along a line of intersection.

Figure 11A:
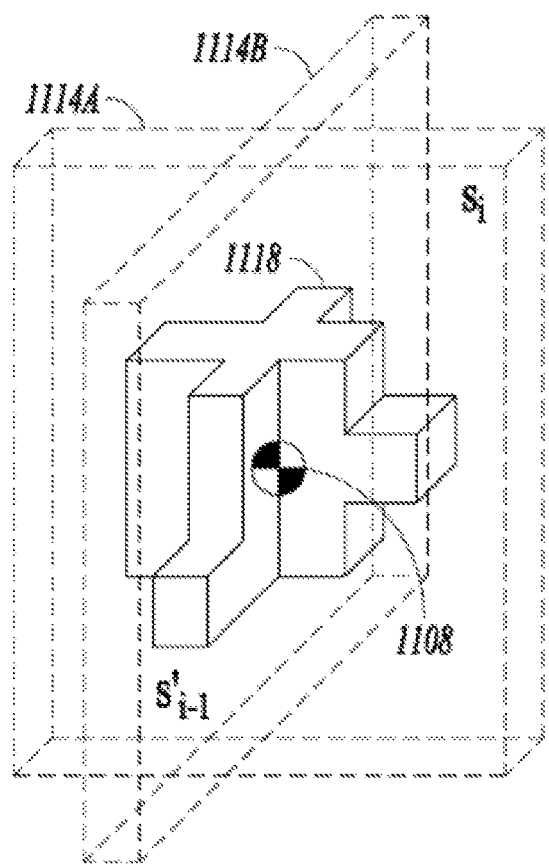
FIG. 11A illustrates generally a composite segmented representation of a target locus, such as after spatial registration of portions of the target locus acquired at different times, according to some embodiments.

FIG. 11A illustrates generally a composite 1118 representation of a target locus, such as after spatial registration of segmented portions of the target locus acquired at different times corresponding to spatially-registered imaging slices 1114A and 1114B. After portions of the target locus from two or more imaging slices have been spatially registered, a feature can be extracted such as from a composite 1118. For example, a location of a centroid 1108 of the composite 1118 or other feature can be determined, such as providing an estimate of a centroid location of the target locus for use in updating a radiation therapy protocol. In another example, a determined spatial displacement between portions of the target locus in the first and second imaging slices 1114A and 1114B can be used to update a radiation therapy protocol.

Figure 11B:
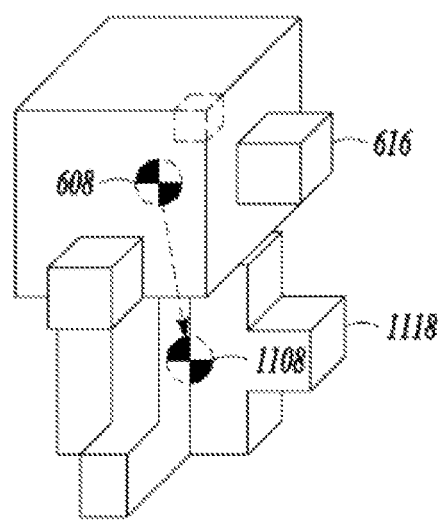
FIG. 11B illustrates generally a technique for determining a difference between a location of the target locus according to acquired spatially-registered imaging information as compared to an earlier location of the target locus such as represented by earlier-acquired volumetric imaging information, according to some embodiments.

FIG. 11B illustrates generally a technique for determining a difference between a later estimated or predicted location of a composite 1118 of the target locus according to acquired spatially-registered imaging information as compared to an earlier location of the target locus 616 such as represented by earlier-acquired volumetric imaging information. A displacement of one or more features can be used to estimate a present or future target locus location. For example, a displacement can be determined between an earlier-determined centroid 608 extracted from the reference imaging information and later-determined centroid 1108. In another example, shift parameters from an imaging registration can be used to provide an updated target locus without requiring extraction or determination of features such as a centroid. Generally, a variety of other techniques can be used such as to extract information indicative of a motion or displacement of the target locus 616 using spatially-registered imaging slices.

For example, once a set of previous imaging slices are aligned to the current slice to form a slice set $S_i$, $S'_{i-1}$, $S'_{i-2}$, . . . $S'_{i-n}$, an optimal registration between the slice set (or a composite 1118 generated from such a slice set) and a three-dimensional reference volume can be found (such as a reference volume corresponding to the target locus 616 as shown in FIG. 11B). As an illustrative example, a sagittal slice acquisition can be preceded by a coronal slice acquisition. A spatial translation can be identified that brings the coronal slice to the same time point as the sagittal slice to spatially register the coronal slice with the sagittal slice. Then, both slices can be established within a 3D voxel coordinate space. This can be done by inserting the slices as infinitesimally thin slices, or as finite slices using the known slice thickness (such as shown in the composite 1118 of FIG. 11A and FIG. 11B).

Voxels that are not filled by portions of the target locus from each slice can be left unfilled. A 3D-to-3D registration can then be determined between the 3D reference image (e.g., corresponding to target locus 616) and the 3D "slice-filled image" (corresponding to the composite 1118). A mask can be used to filter out voxels that have not been filled. In another example, a 3D-to-2D registration can be performed, such as using multiple 2D slices rather than a single composite. For example, shift parameters (e.g., displacement of one or more features such as a centroid or a set of shift values specifying a translation or rotation of region of interest) of the 3D reference image can be evaluated, such as optimizing values of a similarity metric that compares the voxels of the shifted 3D volumetric reference image to each of the slices of the multiple 2D imaging slices, using registration and optimization techniques as mentioned above. In this manner, a 3D-to-2D registration can be performed, such as to identify an optimal set of shift values. A location of the target can be updated using information obtained from the shift values. 3D-to-3D, 2D-to-2D, or 3D-to-2D registration techniques need not require image segmentation (e.g., the target locus itself need not be segmented), and such registration need not require identification of imaging features such as a centroid or edge location. Instead, registration can be performed using grayscale or contrast imaging information (or other extracted values), such as over a specified region of interest generally as mentioned elsewhere herein.

Figure 11C:
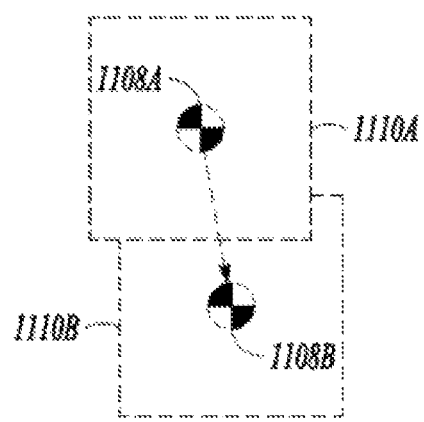
FIG. 11C illustrates generally a technique for updating a therapy protocol, such as to shift a therapy locus to a new location, according to some embodiments.

FIG. 11C illustrates generally a technique for updating a therapy protocol, such as to shift a therapy locus to a new location. An earlier radiation therapy target region 1110A can be established, such as corresponding to a target locus extracted from a volumetric reference image or established according to other treatment or dosimetric objectives. Such a therapy target region 1110A can be established at least in part using one or more of positioning a radiation therapy output, modulating a therapy beam including modulating one or more of intensity or beam shape, or moving the patient using an actuator such as a moveable therapy couch or platform. One or more features can be extracted from the therapy target region, such as a centroid 1108A. An estimated or predicted displacement of the target locus (e.g., a tumor or other structure to be treated) can be determined, such as using other techniques as described herein.

The therapy target region 1110A can be adjusted to provide an updated therapy target region 1110B. For example, if the target locus has been translated due to patient motion, a similar displacement can be applied to the earlier region 1110A to provide an updated therapy target region 1110B. Similarly, if other features are extracted, the therapy target region 1110A can be adjusted using other techniques such as rotation or scaling. In another example, instead of or in addition to adjusting the therapy target region 1110A, other techniques can be used to control therapy, such as gating therapy to inhibit delivery of radiation therapy unless an updated therapy target region 1110B falls within a specified zone. In yet another example, a surrogate signal, such as derived from a sensor output, can be used to gate therapy. For example, a sensor output can be correlated with the location of a feature extracted from imaging slices, such as a centroid location of a target locus within the imaging slices after the imaging slices are spatially-registered. Therapy delivery can be gated in a synchronous manner, such as triggered in response to the sensor output (e.g., such as to deliver therapy at a certain time during a periodic motion such as respiration).

Figure 15:
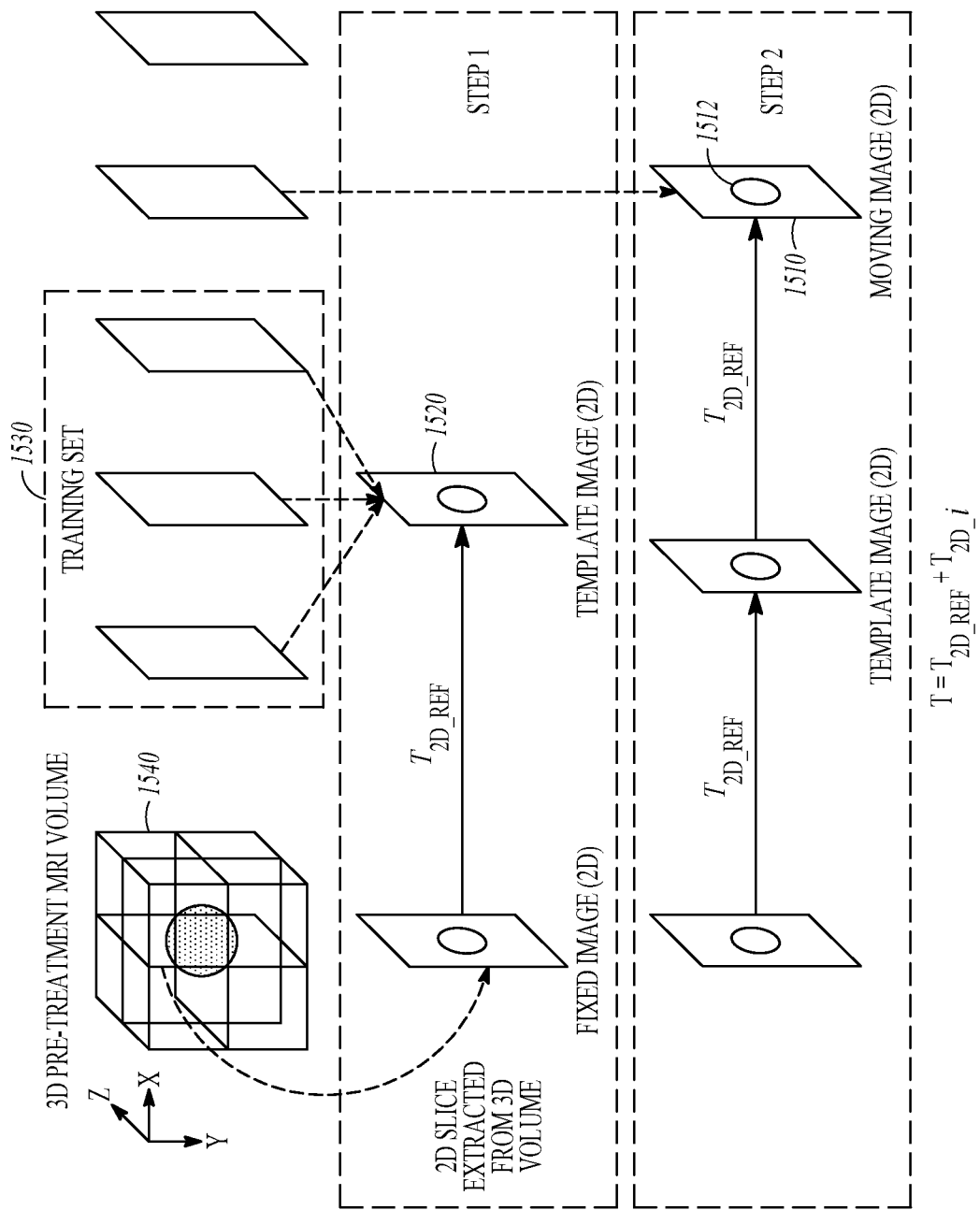
FIG. 15 illustrates a third technique for determining movement of an object, according to some embodiments.

FIG. 15 illustrates a third technique for determining movement of an object, according to some embodiments. For example, as shown in FIG. 15, the radiotherapy processing computing system 510 initially generates a composite (template) imaging slice 1520 that is registered against a corresponding plane of a 3D volumetric image 1540.

Figure 16:
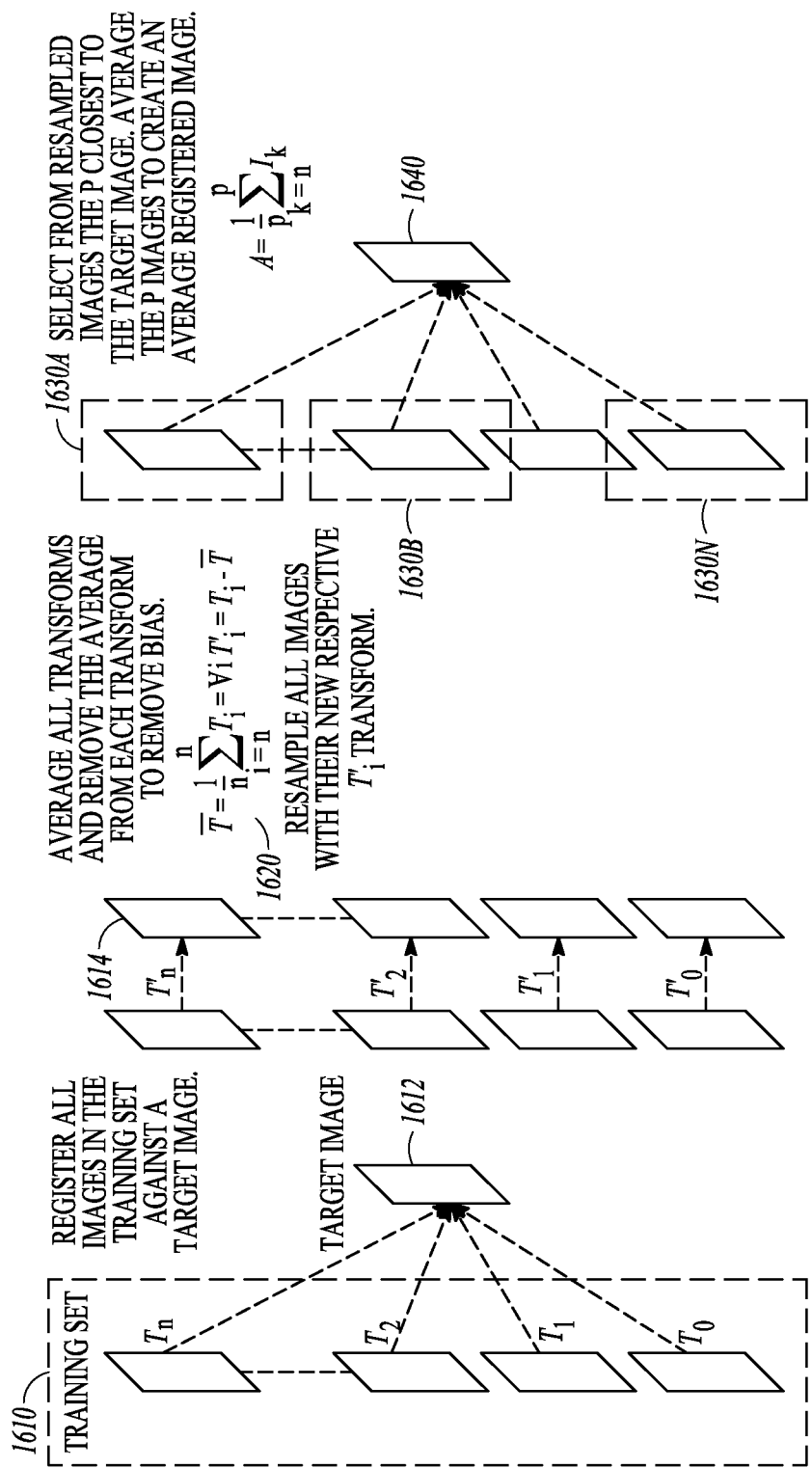
FIG. 16 illustrates a technique for generating a composite slice for determining movement according to the third technique, according to some embodiments.

FIG. 16 shows an illustrative technique for generating the composite imaging slice 1520, according to some embodiments. In some cases, the composite image is generated by averaging a selected subset of imaging slices 1610. For example, a plurality of imaging slices 1610 are obtained prior to activating the radiotherapy beam during the given radiation session. A given slice one of the slices that corresponds to a reference breathing phase (e.g., the end of exhalation) is selected as a target image 1612. The radiotherapy processing computing system 510 deformably registers 1614 a remaining set of the plurality of imaging slices to the selected target image 1612.

The radiotherapy processing computing system 510 averages the deformably registered plurality of imaging slices and determines an average offset 1620 for each of the plurality of imaging slices. The radiotherapy processing computing system 510 resamples the imaging slices based on the average offset to select a subset 1630A-N of the resampled imaging slices based on a distance of each of the resampled imaging slices to the target image (e.g., the selected imaging slice). For example, the radiotherapy processing computing system 510 computes a distance between each of the resampled imaging slices and the target image. The radiotherapy processing computing system 510 selects those imaging slices for which the distances between the slices and the target slice is less than a specified threshold. The composite image 1640 is then generated by averaging the selected subset 1630A-N of the resampled plurality of imaging slices.

Referring back to FIG. 15, after the composite image 1640 is generated, the composite imaging slice 1520 is registered against a new imaging slice corresponding to the same plane as the composite imaging slice to determine movement of the object depicted in the composite imaging slice. As an example, at a first time point during a given radiation session, a first imaging slice 1510 comprising an object 1512 is received. The first imaging slice 1510 may correspond to a first plane (e.g., the sagittal plane). The radiotherapy processing computing system 510 accesses, at the first time point during the given radiation session, a composite imaging slice 1520 corresponding to the first plane. The composite imaging slice is generated using a plurality of imaging slices 1530 that were obtained prior to the first time point. The radiotherapy processing computing system 510 spatially registers the first imaging slice and the composite imaging slice to determine movement of the object. The radiotherapy processing computing system 510 generates an updated therapy protocol to control delivery of a therapy beam based on the determined movement.

In some cases, the radiotherapy processing computing system 510 registers the first imaging slice and the composite imaging slice by mask limiting pixels considered in the registration in one or both of the first imaging slice and the composite imaging slice. In some cases, the composite imaging slice 1520 is registered to the two-dimensional slice extracted from the volumetric image 1540 before the first imaging slice 1510 is registered to the composite imaging slice 1520. In some cases, the composite imaging slice 1520 that is registered to the two-dimensional slice extracted from the volumetric image is manually adjusted to select or change a position or portion of the composite image that is registered relative to the two-dimensional slice.

In some embodiments, similar operations are performed for determining movement based on a composite image along a different plane (e.g., the coronal plane). In such cases, the composite imaging slice 1520 is a first composite image. At a second time point during the given radiation session, the radiotherapy processing computing system 510 receives a second imaging slice that corresponds to a second plane (e.g., a coronal plane). The radiotherapy processing computing system 510 accesses, at the second time point during the given radiation session, a second composite imaging slice (not shown) corresponding to the second plane (e.g., a coronal composite imaging slice). The second composite imaging slice is generated using another plurality of imaging slices obtained prior to the second time point. Specifically, the coronal composite imaging slice is generated in the same manner as that discussed above for the sagittal plane but using slices that are received along the coronal plane. For example, the coronal composite image is generated by averaging a selected subset of coronal imaging slices. For example, a plurality of coronal imaging slices are obtained prior to activating the radiotherapy beam during the given radiation session. A given slice of the coronal slices that corresponds to a reference breathing phase is selected as a target image. In some cases, the same reference breathing phase that is used to select the target image for the first imaging plane (e.g., the sagittal plane) is used to select the target image for the coronal imaging plane. The radiotherapy processing computing system 510 deformably registers a remaining set of the plurality of coronal imaging slices to the selected target image.

The radiotherapy processing computing system 510 averages the deformably registered plurality of coronal imaging slices and determines an average offset for each of the plurality of coronal imaging slices. The radiotherapy processing computing system 510 resamples the coronal imaging slices based on the average offset to select a subset of the resampled coronal imaging slices based on a distance of each of the resampled coronal imaging slices to the target image (e.g., the selected coronal imaging slice). For example, the radiotherapy processing computing system 510 computes a distance between each of the resampled coronal imaging slices and the coronal target image. The radiotherapy processing computing system 510 selects those coronal imaging slices for which the distances between the coronal slices and the target coronal slice is less than a specified threshold. In some cases, the same threshold that is used to select the imaging slices for the first imaging plane (e.g., the sagittal plane) is used to select the imaging slices for the coronal imaging plane. In some cases the thresholds for the different planes are also different. The coronal composite image is then generated by averaging the selected subset of the resampled plurality of imaging slices.

The radiotherapy processing computing system 510 spatially registers the second imaging slice (e.g., the coronal imaging slice) and the second composite imaging slice (corresponding to the coronal plane), including moving a portion of the object in the second imaging slice to register the object in the second imaging slice with a portion of the object in the second composite imaging slice.

Figure 17:
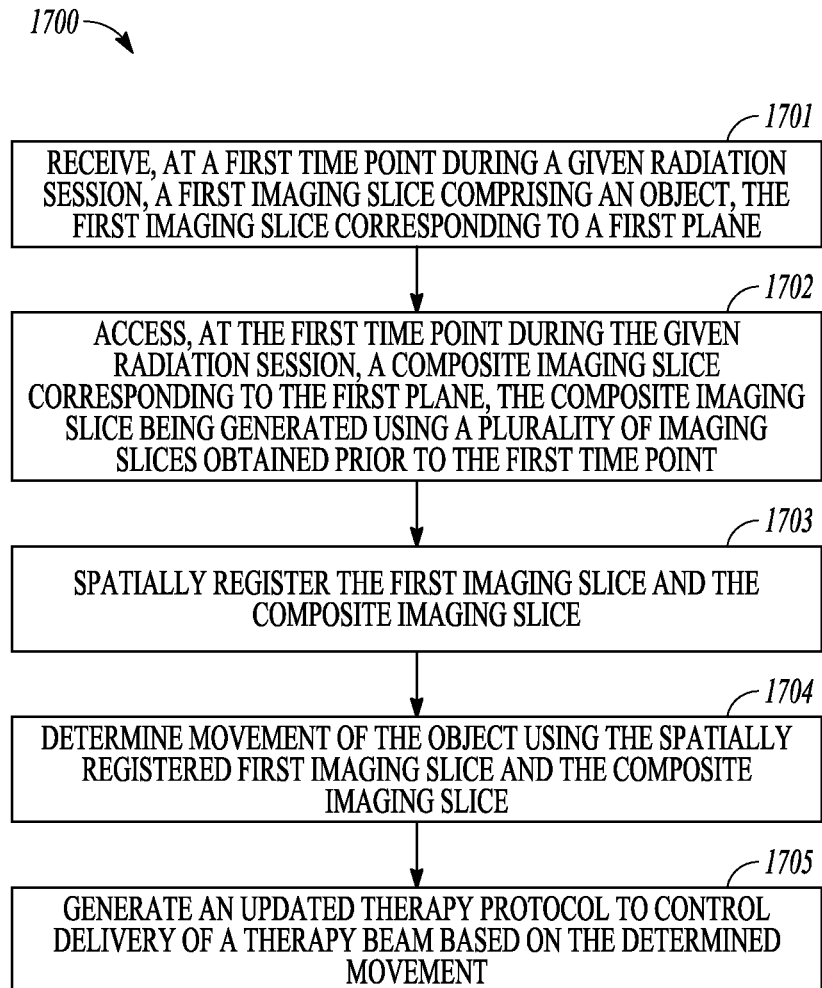
FIG. 17 is a flow diagram for determining movement of the object according to the third technique, according to some embodiments.

FIG. 17 is a flow diagram 1700 for determining movement of the object according to the third technique, according to some embodiments. The operations discussed in FIG. 17 can be performed in sequence, in parallel, skipped, or out of order. The operations discussed in FIG. 17 can be performed by computing system 510 (FIG. 5).

At operation 1701, the computing system 510 receives, at a first time point during a given radiation session, a first imaging slice comprising an object. The first imaging slice corresponds to a first plane (e.g., the sagittal plane).

At operation 1702, the computing system 510 accesses, at the first time point during the given radiation session, a composite imaging slice corresponding to the first plane. The composite imaging slice is generated using a plurality of imaging slices obtained prior to the first time point.

At operation 1703, the computing system 510 spatially registers the first imaging slice and the composite imaging slice. For example, the computing system 510 optimizes a cost function based on differences between the first imaging slice and the composite imaging slices to register the first imaging slice and the composite imaging slice.

At operation 1704, the computing system 510 determines movement of the object using the spatially registered first imaging slice and the composite imaging slice.

At operation 1705, the computing system 510 generates an updated therapy protocol to control delivery of a therapy beam based on the determined movement.

Figure 18:
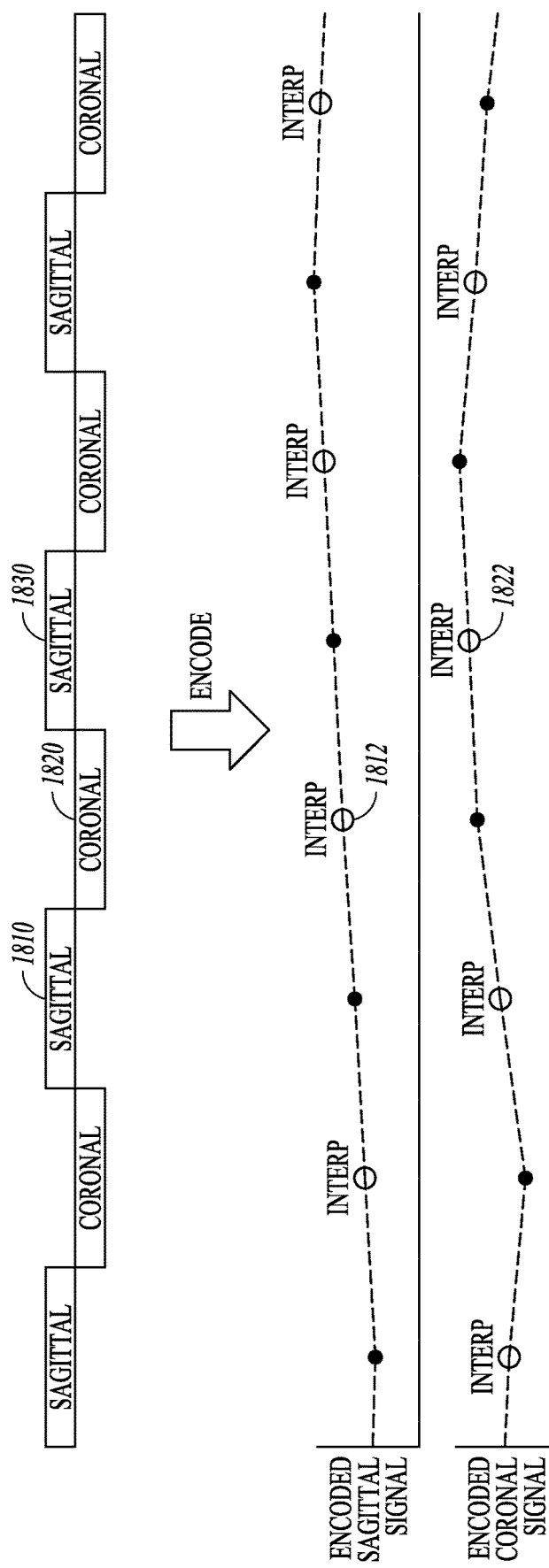
FIG. 18 illustrates a fourth technique for determining movement of an object, according to some embodiments.

FIG. 18 illustrates a fourth technique for determining movement of an object, according to some embodiments. According to the technique shown in FIG. 18, at a first time point in a given radiation session, a first imaging slice 1810 corresponding to a first plane (e.g., a 2D cine image corresponding to or defined along a sagittal plane) is received. The first imaging slice is encoded to a lower dimensional representation (e.g., by converting principal component analysis (PCA) components of a deformable vector field (DVF) of the first imaging slice to estimate the PCA components of the second imaging slice). A trained machine learning model (e.g., a support vector machine or random forest machine, a deep learning neural network model, or neural network or regression technique comprising a support vector machine) is applied to the encoded first imaging slice to estimate an encoded version of a second imaging slice corresponding to a second plane (e.g., the coronal plane) at the first time point to provide a pair of imaging slices for the first time point. As an example, the trained machine learning model is applied to the first imaging slice 1810 (e.g., sagittal plane) to estimate an encoded version of coronal plane imaging slice.

The pair of imaging slices are simultaneously spatially registered to a volumetric image (e.g., a 3D pre-treatment volume of the patient), received prior to the given radiation session to generate an updated therapy protocol to control delivery of a therapy beam based on the calculated displacement of the object. In some cases, prior to registering the images, the estimated encoded version of the second imaging slice is decoded to obtain the second imaging slice at the first time point. The decoded version is then spatially registered together with the first imaging slice 1810 against the volumetric image to determine movement or displacement of the object in three dimensions.

In some embodiments, the machine learning model is trained during an initial period of a radiotherapy fraction, prior to the radiotherapy fraction, or during delivery of the radiotherapy fraction. To train the machine learning model, the radiotherapy processing computing system 510 receives a first sequence of slices 1810 and 1830 (e.g., cine images) along the same plane (e.g., sagittal plane images). The radiotherapy processing computing system 510 also receives a second sequence of slices 1820 (e.g., cine images) along the same plane (e.g., coronal plane images). In some cases, the coronal plane images are received in an alternative manner as the sagittal plane images, such that when a sagittal plane image is received a coronal image is not and vice versa. The radiotherapy processing computing system 510 encodes the first sequence of slices 1810 and 1830 to a lower dimensional representation and interpolates a sagittal image slice 1812 that is between the first sequence of slices 1810 and 1830. The interpolated sagittal image slice 1812 may represent the expected sagittal image slice at the time a coronal image slice 1820 is received. Similar operations are performed to interpolate coronal image slices 1822 to generate an expected coronal image slice when a sagittal image slice is received.

The radiotherapy processing computing system 510 applies the coronal image slice 1820 to the machine learning model to predict a sagittal image slice. During training, the radiotherapy processing computing system 510 computes a deviation between the predicted sagittal image slice and the interpolated sagittal image slice 1812. The radiotherapy processing computing system 510 updates parameters of the machine learning model based on the computed deviation. The radiotherapy processing computing system 510 determines whether the computed deviation satisfies a stopping criterion to determine whether to continue training based on additional coronal image slices or to output the trained machine learning model. Similarly, the radiotherapy processing computing system 510 applies the sagittal image slice 1830 to the machine learning model to predict a coronal image slice. During training, the radiotherapy processing computing system 510 computes a deviation between the predicted coronal image slice and the interpolated coronal image slice 1822. The radiotherapy processing computing system 510 updates parameters of the machine learning model based on the computed deviation. The radiotherapy processing computing system 510 determines whether the computed deviation satisfies a stopping criterion to determine whether to continue training based on additional sagittal image slices or to output the trained machine learning model. In some cases, the machine learning model continues to be updated indefinitely during the radiotherapy treatment session as new sagittal and coronal image slices are received. While sagittal and coronal image counterparts are described as being used to train the machine learning model, any parallel, perpendicular or other angled image slices can be similarly used to train the machine learning model to predict a slice along one angle from a slice received along a different angle.

Figure 19:
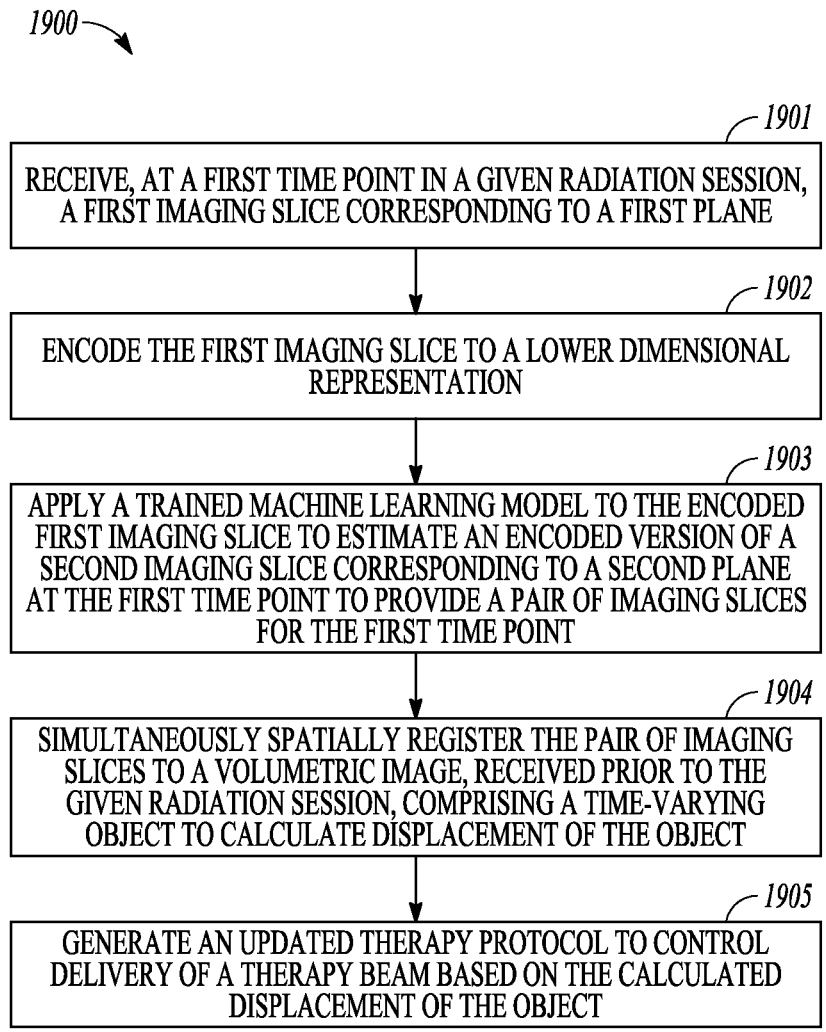
FIG. 19 is a flow diagram for determining movement of the object according to the fourth technique, according to some embodiments.

FIG. 19 is a flow diagram 1900 for determining movement of the object according to the fourth technique, according to some embodiments. The operations discussed in FIG. 19 can be performed in sequence, in parallel, skipped, or out of order. The operations discussed in FIG. 19 can be performed by computing system 510 (FIG. 5).

At operation 1901, the computing system 510 receives, at a first time point in a given radiation session, a first imaging slice corresponding to a first plane.

At operation 1902, the computing system 510 encodes the first imaging slice to a lower dimensional representation.

At operation 1903, the computing system 510 applies a trained machine learning model to the encoded first imaging slice to estimate an encoded version of a second plane at the first time point to provide a set of imaging slices (e.g., a pair of imaging slices) for the first time point. In some cases the set of imaging slices includes three imaging slices that are orthogonal to each other or that are along tilted planes relative to each other.

At operation 1904, the computing system 510 simultaneously spatially registers the set of imaging slices (e.g., the pair of imaging slices) to a volumetric image, received prior to the given radiation session, that includes a time-varying object to calculate displacement of the object. For example, the computing system 510 inserts the set of imaging slices into a 3D volume comprising the volumetric image and fills voxels of the 3D volume where the set of imaging slices intersect the voxels of the 3D volume. As another example, the computing system 510 optimizes a cost function based on differences between the set of imaging slices and the volumetric image.

At operation 1905, the computing system 510 generates an updated therapy protocol to control delivery of a therapy beam based on the calculated displacement of the object.

The techniques (including the second, third, and fourth techniques for determining movement of an object during a given radiotherapy session) described above can be performed in a serial manner, such as including acquiring images and processing such images, then acquiring another series of images, and processing the subsequently-acquired set of images. In another approach, one or more portions of the techniques described herein can be performed in parallel or in an interleaved manner, such as to provide ongoing generation of displacement or other information for use in updating a therapy protocol in an adaptive manner. In some cases, movement of the object can be determined using the third technique (e.g., using a composite image). If movement of the object exceeds a specified threshold, the therapy protocol may immediately be updated. Alternatively, if the movement determined based on the third technique exceeds the threshold, the fourth technique can be applied on the same set of images to determine movement of the object prior to updating the therapy protocol. If the movement of the object again exceeds the specified threshold, the therapy protocol may be updated. In some cases, the third technique may be applied before the fourth technique based on a priority assigned to the third technique. The fourth technique may be skipped and only applied if movement of the object is determined according to the third technique to exceed a specified threshold.

As an illustrative example, the imaging slices are shown as two-dimensional planes that are orthogonal to each other. However, as mentioned in relation to other examples herein, the slices need not be planar nor orthogonal. Each acquired imaging slice can be processed, including processing of one or more slices in parallel with an acquisition of an imaging slice. For example, such processing can include sampled information from a volumetric reference image, such as corresponding to a plane or region of the acquired imaging slice. The extent of a target locus (e.g., a tumor or other anatomical structure that can be used as a landmark for adaptively directing radiation therapy) can be extracted from one or more segmented structures in the volumetric reference image.

A margin can be added to that extent of the target locus, such as to define a region within which the target locus must be located in subsequently-acquired imaging slices. The margin can be adjusted based on factors such as an image acquisition rate (the lower the acquisition rate, the farther the tumor or other target can travel between image acquisitions, and the margin can be correspondingly enlarged). The tumor or other target can be segmented in an acquired imaging slice. Segmented target information extracted from one or more imaging slices can be spatially-registered with the target locus identified in the planning image. Such registration, as described in other examples herein, can be used to determine an updated target locus or to otherwise control or adapt therapy. For example, the updated target locus can be used to gate the treatment, such as pausing the treatment while the updated target locus indicates that the target locus is partially or entirely outside a specified spatial gating window, or the updated target locus can be used to adapt the beam aperture shape to track the tumor, as illustrative examples.

VARIOUS NOTES & EXAMPLES

Each of the non-limiting examples described in this document can stand on its own, or can be combined in various permutations or combinations with one or more of the other examples.

The above detailed description includes references to the accompanying drawings, which form a part of the detailed description. The drawings show, by way of illustration, specific embodiments in which the inventive subject matter can be practiced. These embodiments are also referred to herein as "examples." Such examples can include elements in addition to those shown or described. However, the present inventors also contemplate examples in which only those elements shown or described are provided. Moreover, the present inventors also contemplate examples using any combination or permutation of those elements shown or described (or one or more aspects thereof), either with respect to a particular example (or one or more aspects thereof), or with respect to other examples (or one or more aspects thereof) shown or described herein.

In the event of inconsistent usages between this document and any documents so incorporated by reference, the usage in this document controls.

In this document, the terms "a" or "an" are used, as is common in patent documents, to include one or more than one, independent of any other instances or usages of "at least one" or "one or more." In this document, the term "or" is used to refer to a nonexclusive or, such that "A or B" includes "A but not B," "B but not A," and "A and B," unless otherwise indicated. In this document, the terms "including" and "in which" are used as the plain-English equivalents of the respective terms "comprising" and "wherein." Also, in the following claims, the terms "including" and "comprising" are open-ended, that is, a system, device, article, composition, formulation, or process that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects.

Method examples described herein can be machine or computer-implemented at least in part. Some examples can include a computer-readable medium or machine-readable medium encoded with instructions operable to configure an electronic device to perform methods as described in the above examples. An implementation of such methods can include code, such as microcode, assembly language code, a higher-level language code, or the like. Such code can include computer readable instructions for performing various methods. The code may form portions of computer program products. Further, in an example, the code can be tangibly stored on one or more volatile, non-transitory, or non-volatile tangible computer-readable media, such as during execution or at other times. Examples of these tangible computer-readable media can include, but are not limited to, hard disks, removable magnetic disks, removable optical disks (e.g., compact disks and digital video disks), magnetic cassettes, memory cards or sticks, random access memories (RAMs), read only memories (ROMs), and the like.

The above description is intended to be illustrative, and not restrictive. For example, the above-described examples (or one or more aspects thereof) may be used in combination with each other. Other embodiments can be used, such as by one of ordinary skill in the art upon reviewing the above description. The Abstract is provided to comply with 37 C.F.R. § 1.72(b), to allow the reader to quickly ascertain the nature of the technical disclosure. It is submitted with the understanding that it will not be used to interpret or limit the scope or meaning of the claims. Also, in the above Detailed Description, various features may be grouped together to streamline the disclosure. This should not be interpreted as intending that an unclaimed disclosed feature is essential to any claim. Rather, inventive subject matter may lie in less than all features of a particular disclosed embodiment. Thus, the following claims are hereby incorporated into the Detailed Description as examples or embodiments, with each claim standing on its own as a separate embodiment, and it is contemplated that such embodiments can be combined with each other in various combinations or permutations. The scope of the inventive subject matter should be determined with reference to the appended claims, along with the full scope of equivalents to which such claims are entitled.

What is claimed is:

1. A computer-implemented method of controlling an adaptive radiation therapy delivery system, the computer-implemented method comprising:

receiving, at a first time point during a given radiation session, a first imaging slice comprising an object, the first imaging slice corresponding to a first plane;

accessing, at the first time point during the given radiation session, a composite imaging slice corresponding to the first plane, the composite imaging slice being generated using a plurality of imaging slices obtained prior to the first time point based at least in part on:

selecting a target image from the plurality of imaging slices;

generating a plurality of transforms for a remaining set of the plurality of imaging slices based on the target image; and computing an average of the plurality of transforms for the remaining set of the plurality of imaging slices;

spatially registering the first imaging slice and the composite imaging slice;

determining movement of the object based on spatially registering the first imaging slice and the composite imaging slice and based at least in part on a difference between the first imaging slice and the composite imaging slice; and generating an updated therapy protocol to control delivery of a therapy beam based on the movement.

2. The computer-implemented method of claim 1, wherein the object comprises a tumor in a patient that is a target of the therapy beam, further comprising receiving, prior to the given radiation session, a volumetric image comprising the object having a difference in image contrast between the first imaging slice and one or more slices of the volumetric image.

3. The computer-implemented method of claim 2, further comprising spatially registering the composite imaging slice to a two-dimensional slice extracted along the first plane from the volumetric image.

4. The computer-implemented method of claim 3, wherein registering the first imaging slice and the composite imaging slice comprises mask limiting pixels in one or both of the first imaging slice and the composite imaging slice to limit registration computation to only pixels associated with the object, wherein the composite imaging slice is registered to the two-dimensional slice before the first imaging slice is registered to the composite imaging slice.

5. The computer-implemented method of claim 3, further comprising receiving user input that manually adjusts a position or portion of the composite imaging slice that is registered relative to the two-dimensional slice.

6. The computer-implemented method of claim 1, wherein the composite imaging slice is a first composite image, further comprising:

receiving, at a second time point during the given radiation session, a second imaging slice comprising the object, the second imaging slice corresponding to a second plane;

accessing, at the second time point during the given radiation session, a second composite imaging slice corresponding to the second plane, the second composite imaging slice being generated using another plurality of imaging slices obtained prior to the second time point; and spatially registering the second imaging slice and the second composite imaging slice, including moving a portion of the object in the second imaging slice to register the object in the second imaging slice with a portion of the object in the second composite imaging slice.

7. The computer-implemented method of claim 1, further comprising gathering the plurality of imaging slices prior to activating the therapy beam.

8. The computer-implemented method of claim 7, wherein a given one of the plurality of imaging slices corresponds to a reference breathing phase and is selected as the target image.

9. The computer-implemented method of claim 8, further comprising deformably registering the remaining set of the plurality of imaging slices to the given one of the plurality of imaging slices to generate the plurality of transforms of each of the remaining set of the plurality of imaging slices.

10. The computer-implemented method of claim 9, further comprising:

adjusting the transforms to provide adjusted transforms by removing the average from the transforms of each of the remaining set of the plurality of imaging slices;

resampling the plurality of imaging slices to provide resampled plurality of imaging slices based on the adjusted transforms of each of the remaining set of the plurality of imaging slices;

selecting a subset of the resampled plurality of imaging slices based on a distance of each of the resampled plurality of imaging slices to the given one of the plurality of imaging slices; and generating the composite imaging slice by averaging the subset of the resampled plurality of imaging slices.

11. The computer-implemented method of claim 10, wherein a distance between each of the selected subset of the resampled plurality of imaging slices and the given one of the plurality of imaging slices is less than a distance between a remaining subset of the resampled plurality of imaging slices and the given one of the plurality of imaging slices.

12. The computer-implemented method of claim 1, wherein the composite imaging slice is generated before activating the therapy beam, the first imaging slice is received before activating the therapy beam, and the movement is determined before activating the therapy beam, and wherein the therapy beam is activated after generating the updated therapy protocol.

13. The computer-implemented method of claim 1, wherein the composite imaging slice is updated while the therapy beam is active, the accessing of the composite imaging slice comprises retrieving the updated composite imaging slice, the first imaging slice is received while the therapy beam is active, and the movement is determined while the therapy beam is active.

14. The computer-implemented method of claim 1, wherein the composite imaging slice is generated before activating the therapy beam, the first imaging slice is received after activating the therapy beam, and the movement is determined after activating the therapy beam.

15. The computer-implemented method of claim 1, further comprising:

selecting, based on application of the average to the plurality of transforms, a subset of the plurality of imaging slices based on a distance of each of the plurality of imaging slices to the target image; and averaging the subset of the plurality of imaging slices to generate the composite imaging slice.

16. A non-transitory computer-readable medium comprising non-transitory computer-readable instructions for controlling an adaptive radiation therapy delivery system, the non-transitory computer-readable instructions perform operations comprising:

receiving, at a first time point during a given radiation session, a first imaging slice comprising an object, the first imaging slice corresponding to a first plane;

accessing, at the first time point during the given radiation session, a composite imaging slice corresponding to the first plane, the composite imaging slice being generated using a plurality of imaging slices obtained prior to the first time point based at least in part on:

selecting a target image from the plurality of imaging slices;

generating a plurality of transforms for a remaining set of the plurality of imaging slices based on the target image; and computing an average of the plurality of transforms for the remaining set of the plurality of imaging slices;

spatially registering the first imaging slice and the composite imaging slice;

determining movement of the object based on spatially registering the first imaging slice and the composite imaging slice and based at least in part on a difference between the first imaging slice and the composite imaging slice; and generating an updated therapy protocol to control delivery of a therapy beam based on the movement.

17. The non-transitory computer-readable medium of claim 16, wherein the object comprises a tumor in a patient that is a target of the therapy beam, further comprising operations for receiving, prior to the given radiation session, a volumetric image comprising the object having a difference in image contrast between the first imaging slice and one or more slices of the volumetric image.

18. The non-transitory computer-readable medium of claim 17, further comprising operations for spatially registering the composite imaging slice to a two-dimensional slice extracted along the first plane from the volumetric image.

19. The computer-implemented method of claim 1, further comprising: adjusting the plurality of transforms to provide adjusted transforms by removing the average from the transforms of each of the remaining set of the plurality of imaging slices.

20. The computer-implemented method of claim 19, further comprising:
resampling the plurality of imaging slices to provide resampled plurality of imaging slices based on the adjusted transforms of each of the remaining set of the plurality of imaging slices; and
selecting a subset of the resampled plurality of imaging slices based on a distance of each of the resampled plurality of imaging slices to the target image.

21. The non-transitory computer-readable medium of claim 16, further comprising operations for gathering the plurality of imaging slices prior to activating the therapy beam.

22. The non-transitory computer-readable medium of claim 21, wherein a given one of the plurality of imaging slices corresponds to a reference breathing phase and is selected as a target image.

23. The non-transitory computer-readable medium of claim 22, further comprising operations for:
deformably registering the remaining set of the plurality of imaging slices to the given one of the plurality of imaging slices to generate transforms of each of the remaining set of the plurality of imaging slices;
adjusting the transforms to provide adjusted transforms by removing the average from the transforms of each of the remaining set of the plurality of imaging slices;
resampling the plurality of imaging slices to provide resampled plurality of imaging slices based on the adjusted transforms of each of the remaining set of the plurality of imaging slices;
selecting a subset of the resampled plurality of imaging slices based on a distance of each of the resampled plurality of imaging slices to the given one of the plurality of imaging slices; and
generating the composite imaging slice by averaging the subset of the resampled plurality of imaging slices.

24. The non-transitory computer-readable medium of claim 16, wherein the composite imaging slice is generated before activating the therapy beam, the first imaging slice is received before activating the therapy beam, and the movement is determined before activating the therapy beam, and wherein the therapy beam is activated after generating the updated therapy protocol.

25. The non-transitory computer-readable medium of claim 16, wherein the composite imaging slice is updated while the therapy beam is active, the accessing of the composite imaging slice comprises retrieving the updated composite imaging slice, the first imaging slice is received while the therapy beam is active, and the movement is determined while the therapy beam is active.

26. The non-transitory computer-readable medium of claim 16, wherein the composite imaging slice is generated before activating the therapy beam, the first imaging slice is received after activating the therapy beam, and the movement is determined after activating the therapy beam.

27. A system of controlling an adaptive radiation therapy delivery system, the system comprising:
one or more processors configured to perform operations comprising:
receiving, at a first time point during a given radiation session, a first imaging slice comprising an object, the first imaging slice corresponding to a first plane;
accessing, at the first time point during the given radiation session, a composite imaging slice corresponding to the first plane, the composite imaging slice being generated using a plurality of imaging slices obtained prior to the first time point based at least in part on:
selecting a target image from the plurality of imaging slices;
generating a plurality of transforms for a remaining set of the plurality of imaging slices based on the target image; and
computing an average of the plurality of transforms for the remaining set of the plurality of imaging slices;
spatially registering the first imaging slice and the composite imaging slice;
determining movement of the object based on spatially registering the first imaging slice and the composite imaging slice and based at least in part on a difference between the first imaging slice and the composite imaging slice; and
generating an updated therapy protocol to control delivery of a therapy beam based on the movement.

28. The system of claim 27, wherein the object comprises a tumor in a patient that is a target of the therapy beam, further comprising operations for receiving, prior to the given radiation session, a volumetric image comprising the object having a difference in image contrast between the first imaging slice and one or more slices of the volumetric image.

29. The system of claim 28, further comprising operations for spatially registering the composite imaging slice to a two-dimensional slice extracted along the first plane from the volumetric image.

30. The system of claim 29, wherein registering the first imaging slice and the composite imaging slice comprises mask limiting pixels considered in the registration in one or both of the first imaging slice and the composite imaging slice to limit registration computation to only pixels associated with the object, wherein the composite imaging slice is registered to the two-dimensional slice before the first imaging slice is registered to the composite imaging slice.

31. The system of claim 27, wherein the composite imaging slice is generated before activating the therapy beam, the first imaging slice is received before activating the therapy beam, and the movement is determined before activating the therapy beam, and wherein the therapy beam is activated after generating the updated therapy protocol.

32. The system of claim 27, wherein the composite imaging slice is updated while the therapy beam is active, the accessing of the composite imaging slice comprises retrieving the updated composite imaging slice, the first imaging slice is received while the therapy beam is active, and the movement is determined while the therapy beam is active.

33. The system of claim 27, wherein the composite imaging slice is generated before activating the therapy beam, the first imaging slice is received after activating the therapy beam, and the movement is determined after activating the therapy beam.

34. The system of claim 27, wherein the operations further comprise:
    deformably registering the remaining set of the plurality of imaging slices to the given one of the plurality of imaging slices to generate the plurality of transforms of each of the remaining set of the plurality of imaging slices;
    adjusting the transforms to provide adjusted transforms by removing the average from the transforms of each of the remaining set of the plurality of imaging slices;
    resampling the plurality of imaging slices to provide resampled plurality of imaging slices based on the adjusted transforms of each of the remaining set of the plurality of imaging slices;
    selecting a subset of the resampled plurality of imaging slices based on a distance of each of the resampled plurality of imaging slices to the given one of the plurality of imaging slices; and
    generating the composite imaging slice by averaging the subset of the resampled plurality of imaging slices.

* * * * *